(12) United States Patent
Sachdeva et al.

(10) Patent No.: US 11,813,138 B2
(45) Date of Patent: Nov. 14, 2023

(54) MODULAR ALIGNER DEVICES AND METHODS FOR ORTHODONTIC TREATMENT

(71) Applicant: Rohit C. Sachdeva, Plano, TX (US)

(72) Inventors: Rohit C. Sachdeva, Plano, TX (US); Takao Kubota, Fukuoka (JP); Jitender Vij, Trumbull, CT (US)

(73) Assignee: Memory Medical Systems, Inc., Plano, TX (US)

( * ) Notice: Subject to any disclaimer, the term of this patent is extended or adjusted under 35 U.S.C. 154(b) by 181 days.

(21) Appl. No.: 16/548,843

(22) Filed: Aug. 23, 2019

(65) Prior Publication Data

US 2020/0060797 A1 Feb. 27, 2020

Related U.S. Application Data

(60) Provisional application No. 62/722,319, filed on Aug. 24, 2018.

(51) Int. Cl.
| | | |
|---|---|---|
| *A61C 7/22* | (2006.01) | |
| *A61F 2/50* | (2006.01) | |
| *G16H 20/40* | (2018.01) | |
| *G16H 50/20* | (2018.01) | |
| *G16H 30/40* | (2018.01) | |
| *A61C 5/30* | (2017.01) | |
| *A61C 7/08* | (2006.01) | |
| *A61C 7/10* | (2006.01) | |
| *A61C 19/06* | (2006.01) | |
| *A61F 7/00* | (2006.01) | |
| *A61C 8/00* | (2006.01) | |

(52) U.S. Cl.
CPC .............. *A61C 7/22* (2013.01); *A61C 5/30* (2017.02); *A61C 7/08* (2013.01); *A61C 7/10* (2013.01); *A61C 19/063* (2013.01); *A61F 2/50* (2013.01); *A61F 7/00* (2013.01); *G16H 20/40* (2018.01); *G16H 30/40* (2018.01); *G16H 50/20* (2018.01); *A61C 8/0009* (2013.01); *A61F 2002/502* (2013.01); *A61F 2007/0017* (2013.01)

(58) Field of Classification Search
CPC .... A61C 7/22; A61C 5/30; A61C 7/08; A61C 7/10; A61C 19/063
See application file for complete search history.

(56) References Cited

U.S. PATENT DOCUMENTS

| | | | | |
|---|---|---|---|---|
| 3,407,500 A | * | 10/1968 | Kesling ................. | A61C 7/08 433/6 |
| 3,922,786 A | * | 12/1975 | Lavin .................... | A61C 7/146 433/74 |
| 4,755,139 A | * | 7/1988 | Abbatte ................. | A61C 7/08 433/6 |
| 4,856,991 A | * | 8/1989 | Breads .................. | A61C 7/125 433/24 |

(Continued)

*Primary Examiner* — Nicholas D Lucchesi
(74) *Attorney, Agent, or Firm* — Law Office of Sam Sokhansanj PLLC

(57) ABSTRACT

An aligner assembly for facilitating an alignment of one or more teeth is disclosed. The aligner assembly includes a shell adapted to receive the one or more teeth. The aligner assembly further includes one or more engagement structures configured to be coupled to one of the one or more teeth or the shell. Each engagement structure includes a slot and adapted to engage with the shell for facilitating a reposition of the one or more teeth.

11 Claims, 31 Drawing Sheets

(56) References Cited

U.S. PATENT DOCUMENTS

| | | | | |
|---|---|---|---|---|
| 5,055,039 A * | 10/1991 | Abbatte | A61C 7/146 433/24 |
| 5,186,623 A * | 2/1993 | Breads | A61C 7/08 433/214 |
| 5,328,362 A * | 7/1994 | Watson | A61C 7/08 523/120 |
| 6,183,248 B1 * | 2/2001 | Chishti | A61C 7/08 433/24 |
| 6,309,215 B1 * | 10/2001 | Phan | A61C 9/00 433/24 |
| 6,524,101 B1 * | 2/2003 | Phan | A61C 7/08 433/24 |
| 6,572,372 B1 * | 6/2003 | Phan | A61C 7/08 433/18 |
| 6,607,382 B1 * | 8/2003 | Kuo | A61P 1/02 433/80 |
| 6,830,450 B2 * | 12/2004 | Knopp | B29C 43/56 433/18 |
| 8,439,674 B2 * | 5/2013 | Li | A61C 19/063 433/80 |
| 8,758,009 B2 * | 6/2014 | Chen | A61C 7/08 433/8 |
| 2002/0192617 A1 * | 12/2002 | Phan | A61C 19/003 433/18 |
| 2004/0209218 A1 * | 10/2004 | Chishti | A61C 7/36 433/7 |
| 2006/0188834 A1 * | 8/2006 | Hilliard | A61C 7/08 433/24 |
| 2009/0191502 A1 * | 7/2009 | Cao | A61C 7/002 433/24 |
| 2011/0020761 A1 * | 1/2011 | Kalili | A61C 7/08 433/214 |
| 2011/0136072 A1 * | 6/2011 | Li | A61C 7/14 433/18 |
| 2015/0366637 A1 * | 12/2015 | Kopelman | A61C 7/08 83/13 |
| 2015/0366638 A1 * | 12/2015 | Kopelman | A61C 7/08 264/16 |
| 2017/0007361 A1 * | 1/2017 | Boronkay | A61C 7/002 |
| 2017/0007364 A1 * | 1/2017 | Wu | A61C 7/08 |
| 2017/0007368 A1 * | 1/2017 | Boronkay | A61C 7/146 |
| 2020/0345457 A1 * | 11/2020 | Wu | A61C 7/08 |
| 2021/0236238 A1 * | 8/2021 | Leeson | B33Y 50/02 |

* cited by examiner

MODULAR ALIGNER DEVICES AND METHODS FOR ORTHODONTIC TREATMENT

CROSS-REFERENCE TO RELATED APPLICATIONS

This application is a non-provisional application corresponding to the provisional application No. 62/722,319, filed Aug. 24, 2018. This application is also related to applications titled "Patient-Centered System and Methods for Total Orthodontic Care Management and "Modular Orthodontic Devices and Methods Of Treatment", filed on Aug. 23, 2019, the entire contents of which are incorporated by reference herein.

FIELD OF THE INVENTION

The present invention generally relates to aligner assemblies, more particularly to an aligner assembly having a removable tray adapted to be secured to a plurality of teeth or a single tooth with or without one or more attachments coupled to one or more teeth. The aligner assemblies are designed to provide a more controlled, predictable efficient and effective orthodontic tooth movement with the use of shells and attachments. Furthermore, the aligner assemblies are designed to cause less pain and discomfort to the patient, are safer to use, address the patient's aesthetic demands and are biofriendly.

BACKGROUND ART

Conventional fixed orthodontic appliances include the use of brackets and wires to move teeth. Brackets are bonded to the patient's teeth and act as handles to hold the wires. The wires are deformed to engage the brackets, and as the wires recover elastically towards their original shape, the wires exert forces on the teeth. These forces create a biological response that facilitate the movement of teeth to move through bone. Through the care cycle, the practitioner controls the applied forces and therefore orthodontic tooth movement by making a series of adjustments to the wires and repositioning of the brackets to achieve the planned outcome.

In recent years, orthodontists have adopted the use of aligners to provide orthodontic treatment. Aligners are preformed removeable plastic shells that envelope the entire surfaces of the tooth crowns. aligners are commonly used with attachments bonded to teeth to deform the pre-configured shells on the teeth to generate tooth moving forces. Over the course of the treatment, a patient will wear multiple aligners to achieve tooth alignment. Forces generated by the aligners cannot be effectively controlled. Additionally, aligners cannot create pull forces and are therefore they are not as effective in controlling certain types of orthodontic tooth movement, such as, extrusion or space closure. Also, severe tooth rotations are extremely difficult to correct with aligners since they do not grip the teeth effectively and therefore cannot impart rotational forces as effectively. Furthermore, aligners are limited in generating torqueing couples predictably. Aligners coupled with one or more attachments bonded to the teeth can provide for some additional control of the forces applied.

As multiple aligners are used over time both systemic and random errors of the design and manufacturing processes aggregate and are reflected in unwanted tooth movement. Currently, options to predictably adjust aligners to generate controlled forces at the chairside remain limited. The doctor is commonly compelled to reorder a new set of aligners when the teeth do not track to a plan. This results int increased costs of treatment and impacts patient satisfaction and at an environmental level increases plastic pollution. Furthermore, with current aligners the patient has few options to affect the design of aligners to achieve the look they wish to have. Also, since aligners are worn for most of the day, they do not allow for the saliva to have a washing effect on the teeth and this may increase the risk of the patient developing caries and/or white spot lesions on the teeth and also effect the smell of the patients breath. Frequent changes of the aligners and their sharp edges of the aligners commonly add to the patients discomfort and therefore impact the patient's adherence and persistence in wearing the appliance. When the patient does not wear the aligners as per plan, the treatment is delayed, and quiet often the aligner is lost. Furthermore, a range and rate of orthodontic tooth movement when using an aligner is substantially limited by the design constraints build into the aligner and the response of the biological system. Approaches to accelerate tooth movement using lasers and vibration have been conventionally used, but they add substantially to the cost of care and their benefits remain controversial. Also, current aligners are limited in simultaneously correcting a position of the jaw bones as the teeth are aligned. In light of the above discussion, there is required an improved aligner that overcomes the above mentioned deficiencies.

SUMMARY OF THE INVENTION

According to a first aspect of the present disclosure an aligner assembly for facilitating an alignment of one or more teeth is disclosed. The aligner assembly includes a shell adapted to receive the one or more teeth. The aligner assembly further includes one or more engagement structures configured to be coupled to one of the one or more teeth or the shell. Each engagement structure includes a slot and adapted to engage with the shell for facilitating a repositioning of the one or more teeth.

According to another aspect of the present disclosure an aligner assembly for facilitating a repositioning of one or more teeth is disclosed. The aligner assembly includes an inner shell adapted to be positioned the one or more teeth and an outer shell adapted to be positioned over the inner shell. The aligner assembly further includes one or more engagement structures extending from one of the inner shell or the outer shell and adapted to apply a force on the one or more teeth to facilitate a movement of the one or more teeth.

An orthodontic appliance is disclosed according to yet another aspect of the disclosure. The orthodontic appliance includes a shell adapted to receive one or more teeth for facilitating an alignment of the one or more teeth. The orthodontic appliance further includes an attachment coupled to the shell and adapted facilitate a second movement of the one or more teeth.

BRIEF DESCRIPTION OF THE DRAWINGS

At least one example of the invention will be described with reference to the accompanying drawings, in which.

DETAILED DESCRIPTION OF THE EMBODIMENTS

Figure 1A:
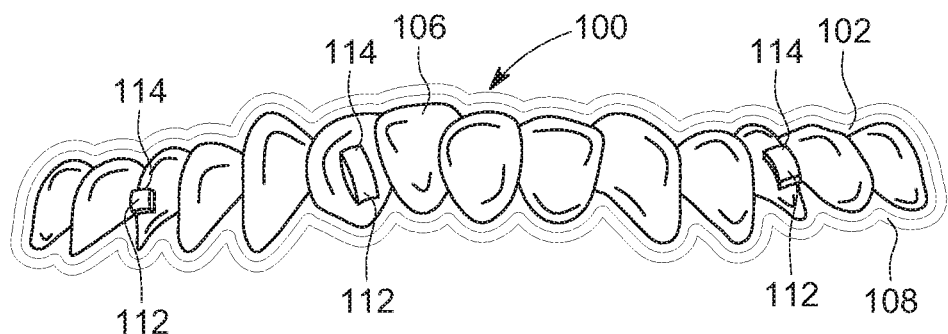
FIG. 1A illustrates an aligner assembly, in accordance with an embodiment of the present invention.
Figure 1B:
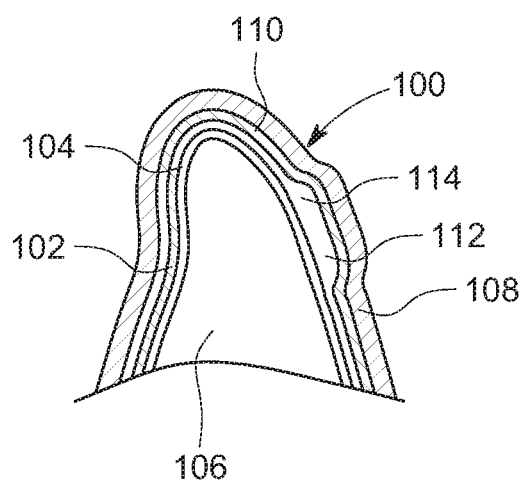
FIG. 1B illustrates a sectional view of the aligner assembly of FIG. 1A, in accordance with an embodiment of the present invention.

Referring to FIGS. 1A and 1B, an aligner assembly 100 according to an exemplary embodiment is shown. The aligner assembly 100 includes an inner shell 102 and an outer shell 108 adapted to be disposed over the inner shell 102. The inner shell 102 has one or more first cavities 104 for being removably positioned for receiving teeth 106 of a patient and facilitates a repositioning of teeth 106. The inner shell 102 may be a continuous shell or a segmented shell covering teeth 106 The design and fabrication of the inner shell 102 or the outer shell 108 is well known for those skilled in the art. The inner shell 102 can be designed to fit over all teeth or a selected number of teeth in an upper jaw and/or a lower jaw. Further, the outer shell 108 has a plurality of second cavities 110 shaped to receive teeth 106. The outer shell 108 is adapted to be removably positioned over the inner shell 102, and may be shaped to generate one or more forces and/or couples on the teeth to reposition the teeth 106 to an intermediate position or a final position. The inner shell 102 and the outer shell 108 are both designed to accommodate for the incremental movement of the teeth towards their intermediate or final position. final. Further, a profile of an inner surface of the outer shell 108 may have a different position and/or orientation than a profile of an outer surface the inner shell 102 to apply forces on the teeth 106 to reposition the teeth 106. In this manner, only the outer shell 108 is changed during the course of treatment, while the inner shell remains same, and thereby minimizing the number of attachments bonded directly to the teeth.

Further, in some embodiments, the aligner assembly 100 may include one or more engagement structures 112, such as, protrusions or recesses. In an embodiment, the engagement structures 112 may be protrusions 114 extending outwardly from the outer surface of the inner shell 102. As shown, the protrusions 114 may extend outwardly in a direction away from the tooth 106 when the inner shell 102 is positioned on the teeth 106. When the outer shell 108 is positioned over the inner shell 102, the protrusions 114 are pushed against the outer shell 108, resulting into a deformation of the outer shell 108 and hence a force is applied on the tooth 106 to enable a desired tooth movement. Further, in an embodiment, the inner shell 102 and/or the outer shell 108 may include appropriate recesses to facilitate movement of teeth 106. In certain other implementations (not shown), the inner shell 102 may include protrusions extending from an inner surface of the inner shell 102. Alternatively, the outer shell 108 may include the engagement structures formed on an inner surface of the outer shell 108 and extending inside the cavities 110 from the inner surface of the outer shell 108. In such cases, the protrusions may extend inwardly in a direction towards the tooth 106, when the outer shell 108 is positioned over the inner shell 102. In an embodiment, the engagement structures 112 may be integrally formed with the inner shell 102 or the outer shell 108. In an embodiment, the engagement structures 112 may be removably coupled to the inner shell 102 and/or the outer shell 108. In such a case, the engagement structures 112 may be incrementally changed during the course of the treatment to incrementally reposition the teeth to a final position. The engagement structures 112 may be removably attached to the inner shell 102 or the outer shell 108 by using pressure sensitive tapes, by bonding with adhesive, welding, or any other mechanical attachment means known in the art. Adhesive may be a medical grade adhesive, and may include one or more of synthetic rubber adhesive, acrylate adhesive, silicone pressure sensitive agents, soft silicone gel adhesive. The adhesive may be applied to backing layers having one or more of polyurethane, polyethylene, polyester, or any other suitable material known in the art.

Also, the material, number, location, size, shape, and an inclination of the engagement structures 112 may be varied depending on the nature and type of orthodontic tooth movement and the magnitude of force to be applied on the teeth 106 and/or a desired line of action of force to obtain a desired movement of the teeth 106 and/or a desired point of application of force and/or a desired direction of force to achieve a desired tooth movement. Further, it may be envisioned that the inner shell 102 and/or the outer shell 108 may be sectioned along a length to be positioned over any number of teeth with intermediate teeth being not covered by the aligner assembly 100.

Furthermore, in some embodiments, the aligner assembly 100 may include one or more stabilizing structures (not shown) to stabilize the inner shell 102 with the teeth 106 or stabilize the outer shell 108 on the inner shell 102. In an embodiment, the stabilizing structures may be attached to teeth 106 to stabilize the inner shell 102 with the teeth 106. In another embodiment, the stabilizing structures may be attached or formed into the outer shell 108 to stabilize the outer shell 108 with the inner shell 102. In an embodiment, the stabilizing structures may be recesses formed into a wall of the outer shell 108. Also, the stiffness and thickness of the outer shell 108 may be different from the stiffness and thickness of the inner shell 102. In an embodiment, the stiffnesses, size, and shape of the engagement structures 112 may be different from each other and may be different form that of the inner shell 102 and/or the outer shell 108. In an embodiment, the stiffness of the engagement structures 112, the inner shell 102, and the outer shell 108 may be incrementally changed during the course of treatment. Also, in an embodiment, a stiffness of only one section of the inner shell 102 may be changed when the inner shell 102 is formed by joining the one or more sections. Similarly, a stiffness of only one section of the outer shell 108 may be changed when the outer shell 108 is formed by joining the one or more sections. In this manner, by using the aligner 100 assembly having two shells 102, 108, the number of attachments need to be attached to teeth 106 for aligning the teeth 106 are minimized. In an embodiment, when the engagement structures 112 are made on the outer shell 108, the inner shell 102 may include a window/cut-out to allow for a direct contact of the engagement structures 112 with the teeth 106. Further, the inner shell 102 and/or the outer shell 108 or the teeth 106 may include location marking to facilitate a positioning of the engagement structures 112. In an embodiment, a size and a shape the engagement structures 112 for subsequent repositioning of the teeth 106 may be changed by attaching one or more shims of suitable dimensions and sizes to an existing engagement structure. In an embodiment, the one or more shims may be attached to an inner surface or an outer surface of the inner shell 102 or the outer shell 108 to form the engagement structures 112. In an embodiment, the size and dimension of the subsequent shims may be decreased or increased. Further, the shims may made of thermoplastic material, elastomers, composites, or any other suitable material known in the art.

Figure 2A:
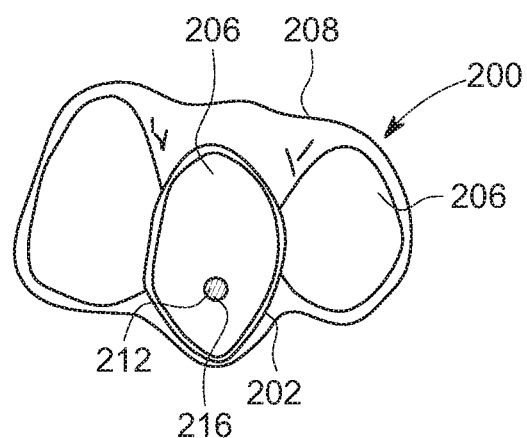
FIG. 2A illustrates an aligner assembly, in accordance with an embodiment of the present invention.
Figure 2B:
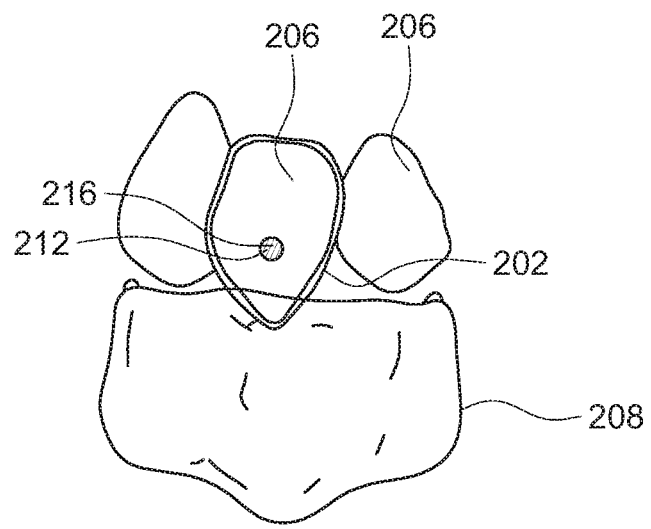
FIG. 2B illustrates an inner shell and an outer shell of the aligner assembly of FIG. 2A, in accordance with an embodiment of the present invention.
Figure 2C:
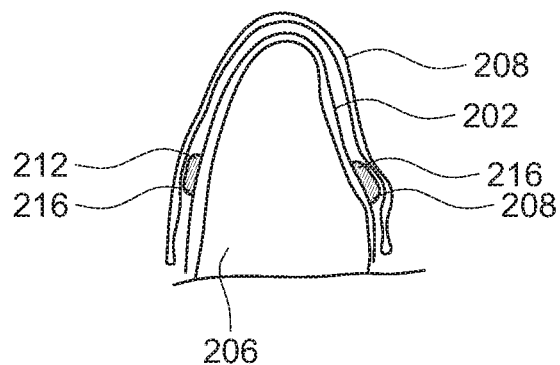
FIG. 2C illustrates a sectional view of the aligner assembly of FIG. 2A in accordance with an embodiment of the present invention.

Referring to FIGS. 2A, 2B, and 2C, an exemplary aligner assembly 200 similar to the aligner assembly 100 is shown. The aligner assembly 200 has one or more engagement structures 212 in a shape of circular protrusions 216. As illustrated, the aligner assembly 200 includes the inner shell 202 having an outer surface, an inner surface, and the one or more engagement structures 112 as circular protrusions 216. Further, the aligner assembly 200 has an outer shell 208 adapted to be positioned over the inner shell 202. As the outer shell 208 is positioned over the inner shell 202, the engagement structures 212 are elastically deformed, thereby applying a force or torque on the tooth 206 to reposition the tooth 206. In an embodiment (not shown), the inner shell 202 may include two engagement structures 212 that may apply force or torque on a single tooth. In such a case, the two engagement structures 212 are disposed offset from each other to apply a torque on the tooth.

Figure 3A:
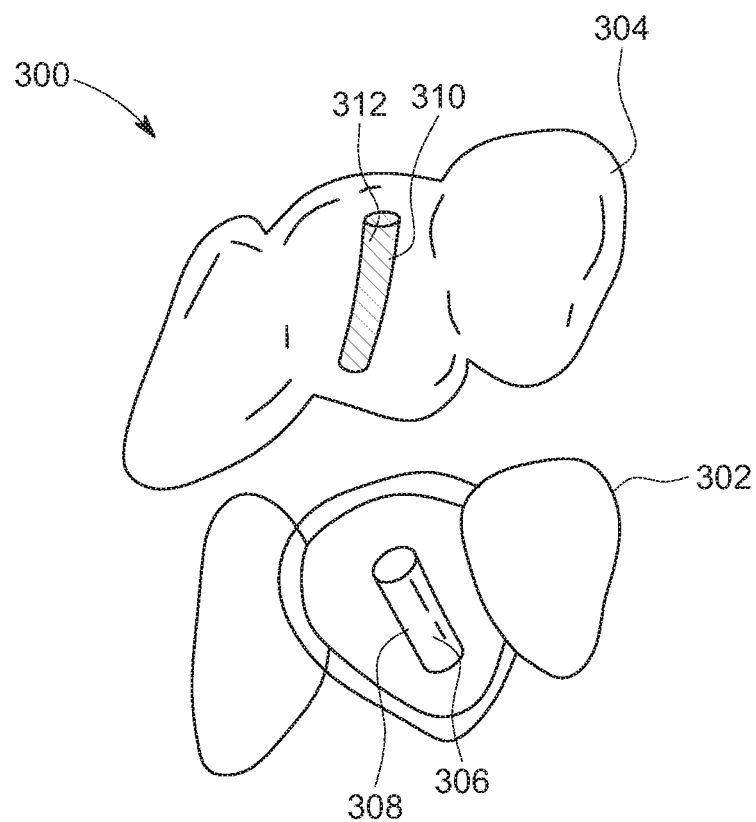
FIG. 3A illustrates an aligner assembly having an inner shell and an outer shell, in accordance with an embodiment of the present invention.
Figure 3B:
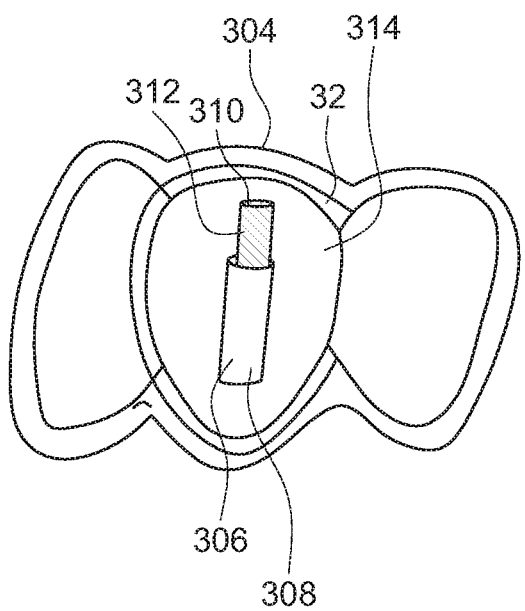
FIG. 3B illustrates the aligner assembly of FIG. 3A disposed over one or more teeth, in accordance with an embodiment of the present invention.

Referring to FIGS. 3A and 3B, another exemplary aligner assembly 300 having an inner shell 302 and an outer shell 304 is shown. The inner shell 302 may include one or more engagement structures 306 disposed on an outer surface of the inner shell 302. As illustrated, the engagement structure 306 includes a female receptacle shaped as hollow cylinder 308 adapted to receive a complimentary male structure. Further, the outer shell 304 may include a cooperating structure 310 disposed at an inner surface of the outer shell 304. In an embodiment, the cooperating structure 310 may integrally formed with the outer shell 304. In another embodiment, the cooperating structure 310 may removably attached to the outer shell 304. In such a case, the cooperating structures 310 may be incrementally changed during the course of the treatment to incrementally reposition the teeth to a final position. The cooperating structure 310 may be attached to an inner surface of the outer shell 304 by pressure adhesive taps, by welding, or bonding by mechanical means, or any other means known in the art. In an embodiment, the cooperating structure 310 may be made of materials with different chemical, mechanical, and physical characteristics such as, shape memory alloys, fiber reinforced composite, or elastomers, or others acceptable material suitable for use in a mouth of the patient. In an embodiment, the cooperating structure 310 may include a stiffness different from a stiffness of the rest of the outer shell 304, and may be formed of fiber reinforced composite. In Further, it may be understood that an engagement of the engagement structure and the cooperating structure cause a force to act on the one or more teeth to enable a movement and repositioning of one or more teeth.

As illustrated, the cooperating structure 310 may be a cylindrical pin 312 adapted to be inserted, at least partly, into the hollow cylinder 308 of the inner shell 302. A relative orientation of the hollow cylinder 308 and the cylindrical pin 312 may be selected so as to apply a desired amount of force and/or torque on tooth 314 in a desired direction. In response of insertion of the cylindrical pin 312 inside the hollow cylinder 308, a force or torque is applied on the tooth 314 to reposition the tooth 314 to an intermediate position or a final position. In this manner, a series of the outer shell 304 having the cooperating structure 310 of different size, material, dimensions, orientation, etc. may be utilized to reposition the tooth 314 to the final position. Further, numbers and locations of the engagement structures 306 and the cooperating structures 310 may also be varied.

Figure 3C:
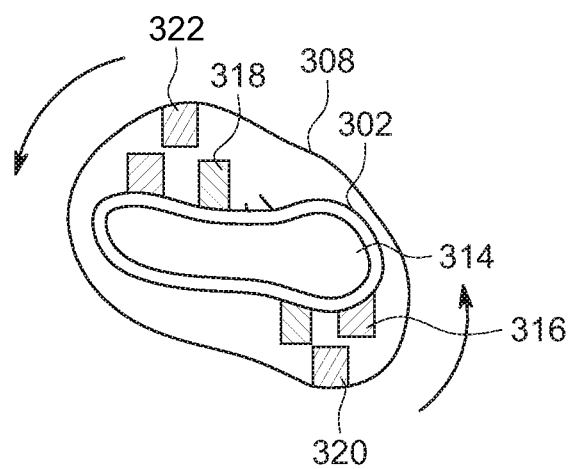
FIG. 3C illustrates the aligner assembly of FIG. 3A having two engagement structures and two cooperating structures, in accordance with an embodiment of the present invention.

In an embodiment (as shown in FIG. 3C), the inner shell 302 may include a first engagement structure 316 extending outwardly from a front wall of the inner shell 302 and a second engagement structure 318 extending outwardly from a rear wall of the inner shell 302. As shown, the first engagement structure 316 and the second engagement structure 318 are offset laterally from each other and adapted to apply a couple or torque on a single tooth when the inner shell 302 and the outer shell 304 are positioned over the teeth of the patient. The first engagement structure 316 and the second engagement structure 318 are adapted engage with a first cooperating structure 320 and a second cooperating structure 322 respectively. Dimensions, materials, inclinations, orientations of the engagement structures 316, 318 and the cooperating structures 320, 322 can be changed.

Figure 4A:
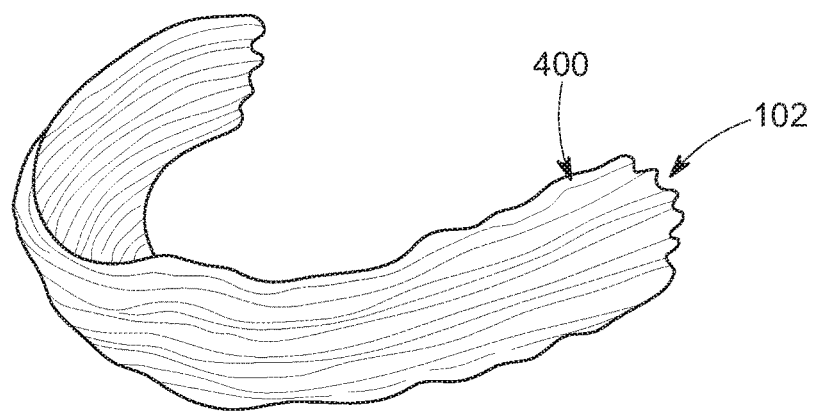
FIG. 4A illustrates a shell having a corrugated structure, in accordance with an embodiment of the present invention.
Figure 4B:
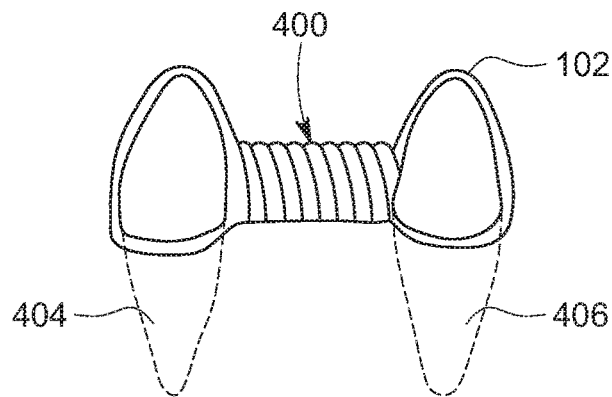
FIG. 4B illustrates the shell of FIG. 4A disposed over the teeth, in accordance with an embodiment of the present invention.
Figure 4C:
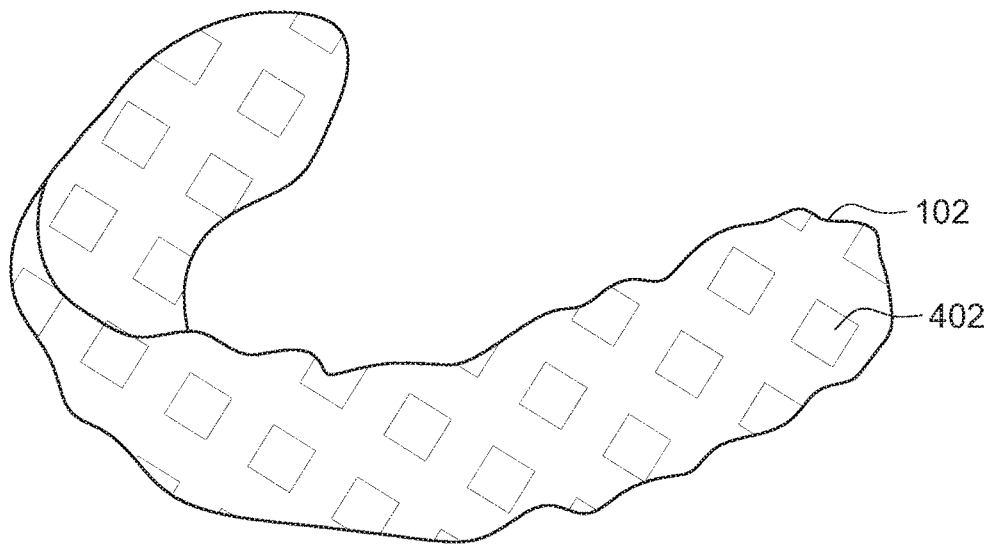
FIG. 4C illustrates a shell having a honeycomb structure, in accordance with an embodiment of the present invention.

In certain embodiments, the inner shell 102 and/or the outer shell 108 may be designed and manufactured directly using additive manufacturing techniques, for example stereolithography. The inner shell 102 and/or the outer shell 108 may be printed to include a corrugated structure or a honeycomb structure to change the stiffness. In an embodiment, the inner shell 102 and/or the outer shell 108 may include a plurality of laminated structures that are preferentially oriented and located to change the stiffness. In embodiment, the laminated structures may be made of different material. An exemplary inner shell 102 having a corrugated structure 400 is shown in FIGS. 4A and 4B. In an embodiment, the corrugation may extend in multiple directions so that the inner shell 102 may include different stiffness in different directions. In an embodiment, the corrugation may extend in a horizontal direction, a vertical direction, or any other direction. The corrugated structure 400 may result in relatively high strength to weight ratio. In certain embodiments, as shown in FIG. 4B, the corrugated structure 400 may be attached to adjacent teeth 404, 406 in compression to create a push force on the adjacent teeth 404, 406 to open space, and thereby facilitates a repositioning of the teeth 404, 406 without using any additional attachments. Also, an inner shell 108 having a honeycomb structure 402 is shown in FIG. 4C. The honeycomb structure 402 may facilitate in reduction in amount of material required for manufacturing the shell (the inner shell 102 and/or the outer shell 108). In an embodiment, the honeycomb structure may extend in a horizontal direction, a vertical direction, or any other direction. Also, a size, dimensions, and/or orientation of the pores of the honeycomb structure 402 may vary. In certain embodiment, the inner shell 102 and/or the outer shell 108 may include walls of variable thickness to generate the desired forces. Furthermore, the inner shell 102 and/or the outer shell 108 may be printed directly or using prefabricated sheets with thermoforming or vacuum (pressure) forming techniques well known to those skilled in the art. In an embodiment, the inner shell 102 and/or the outer shell 108 may include one or more multilayered structures. The multilayered structures may be formed by using 3-dimensional printing or any other manufacturing techniques known in the art. The size, dimensions, and/or and orientation of each multilayered structure may be selected to provide different stiffness in different segments of the inner shell 102 and/or the outer shell 108. In an example, a flexural modulus of at least a part of the inner shell 102 or outer shell 108 may be in a range of 25 million pounds per square inch to 45 million pounds per square inch. In an example, a hardness at least a part of the inner shell 102 or outer shell 108 may be in a range of 50A to 100D.

In certain embodiments, the outer shell 108 and/or the inner shell 102 may include a coating of one or more materials to prevent halitosis and/or minimize pain, gum inflammation, decalcification of teeth. In an embodiment, the coating may include anti halitosis agents, for example, a zinc compound salt, such as, but not limited to, zinc chloride (0.5-2 percent), zinc sulfate, zinc carbonate, zinc acetate, zinc gluconate, zinc citrate, any other zinc salt that can release zinc ion, at least one amino acid, and at least one ascorbic acid. In an embodiment, the coating may include anti-decalcification agents, such as a compound containing five percent sodium fluoride or 0.40-0.50 percent stannous fluoride, etc. In an embodiment, the coating may include one or more bleaching agents having one or more of peroxides, metal chlorites, perborates, percarbonates, peroxyacids, etc. The coating may be provided on one or more walls of the inner shell 102 and/or the outer shell 108. A composition of the coating may be changed for subsequent shells 102, 108 during a course of treatment. Also, composition of the coating may differ from one region of the shells 102, 108 to another region of the shells 102, 108. In an embodiment, the coating may also facilitate whitening of teeth. In some embodiments, the coating may include flavoring material, such as, mint that can be selected by the patient. In an embodiment, the coating may be provided on the inner surface and/or the outer surface of the shell 102, 108. In an embodiment, microcapsules or thin film strips may be embedded in the coatings for carrying pharmaceutical materials of flavoring agents. In an embodiment, the coating may include blends of poly-butyl methacrylate (PBMA) and polyethylene vinyl acetate (PEVA) polymers. A delivery rate of various substances embedded or present in the coating may be controlled/varied by changing blend ratio of poly-butyl methacrylate (PBMA) and polyethylene vinyl acetate (PEVA) polymers. In an embodiment, the inner shell 102 and/or the outer shell 108 may include probiotic material. In an embodiment, the probiotic material may be applied as coating, or a thin film strip, or may be embedded as microcapsules. In an embodiment, the probiotic material may include one or more of *S. salivarius* K12 (BLIS K12), *S. salivarius* M18, *L. salivarius, W. cibaria*, etc. In an embodiment, the coating may include antifriction properties to allow easy sliding of the shells 102, 108. In an embodiment, the inner shell 102 and/or the outer shell 108 may include antibiotic material for reducing or preventing inflammation. In an embodiment, the antibiotic material may be applied as coating, or a thin film strip, or may be embedded as microcapsules. In an embodiment, the antibiotic material may include minocycline or doxycycline to control inflammation, or agents such as chlorohexidine gluconate (0.010-0.20 percent chlorhexidine) to control inflammation and bad breath, or essential oils such as eucalyptol. In another embodiment, the coating may incorporate an analgesic such as 5 to 10 percent lidocaine to control pain. Further, any of the anti-decalcification, anti halitosis agents, bleaching agents may be applied as thin film strip or embedded as microcapsules. Further, it may be appreciated that the any of the anti-decalcification, anti halitosis, bleaching agents, probiotics, antibiotics, analgesics, flavoring substances, etc., may be incorporated in any of the components of the aligner assembly, and the concentration of the materials may be varied from one component to another component and from one location to another location within the same component.

Also, in certain implementations, the outer shell 108 and/or the inner shell 102 may include rounded edges. to facilitate a smooth insertion or removal of the inner shell 102 and/or the outer shell 108 from the patient mouth.

Figure 5A:
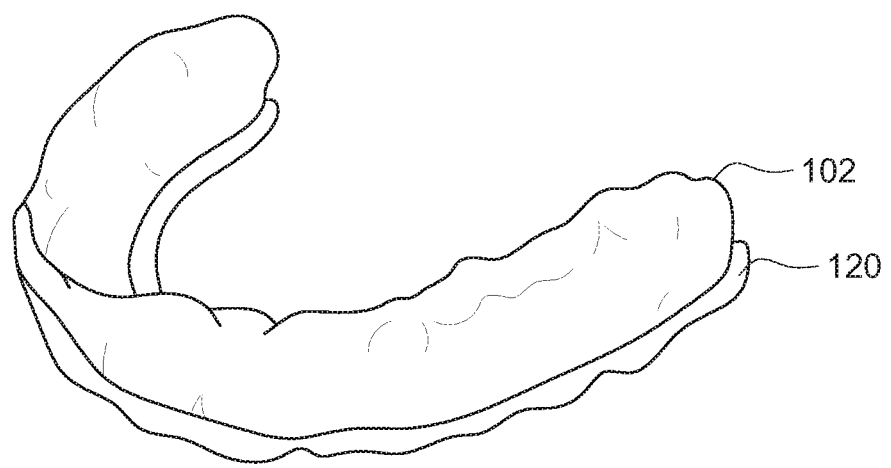
FIG. 5A illustrates an aligner assembly having a sleeve engaged with one or more edges of a shell, in accordance with an embodiment of the present invention.
Figure 5B:
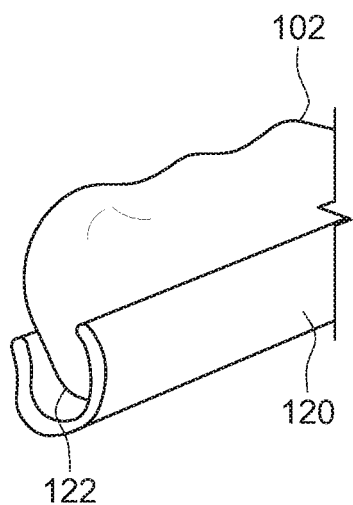
FIG. 5B illustrates a sectional view of the aligner assembly of FIG. 5A, in accordance with an embodiment of the present invention.

In some embodiments, as shown in FIGS. 5A and 5B, the aligner assembly 100 may include one or more removable sleeves 120 to receive one or more edges 122 of the inner shell 102. The sleeve 120 may include adhesive to facilitate an attachment to the edges 112 of the inner shell 102. In an embodiment, the sleeve 120 may be made of polyethelene. Further, the sleeve 120 may include one or more materials to prevent fouling smell. The one or more sleeves 120 may prevent a contact of sharp edge with the tissues of mouth of the patient, and therefore minimize any abrasions or cuts in the patient mouth. Similarly, the aligner assembly 100 may include one or more sleeves (not shown) for receiving one or more sharp edges of the outer shell 108. In an embodiment, the aligner assembly 100 may include one or more gripping ridges (not shown) to facilitate removal of the shell 102 or the shell 108.

Figure 6A:
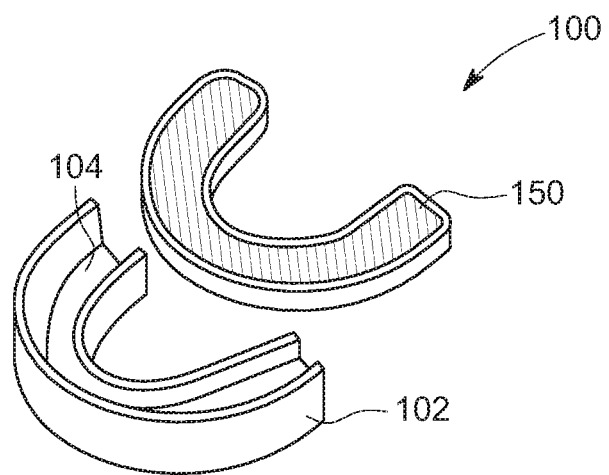
FIG. 6A illustrates an aligner assembly having a thermal pack, in accordance with an embodiment of the present invention.
Figure 6B:
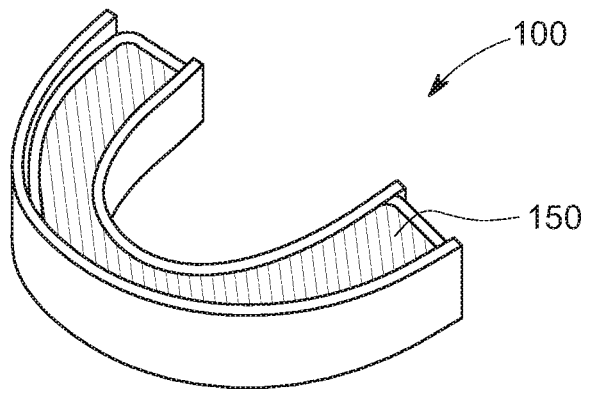
FIG. 6B illustrates an aligner assembly having a thermal pack, in accordance with an embodiment of the present invention.

Further, in certain embodiments, as shown in FIGS. 6A and 6B, the aligner assembly 100 may include a thermal pack 150 that may be disposed between the teeth 106 and the inner shell 102 and/or between the inner shell 102 and the outer shell 108. In an embodiment, the thermal pack 150 may be a cold pack to provide comfort to a wearer of the aligner assembly 100 by decreasing inflammation. In an embodiment, the cold packs may be attached to the shell 102 and/or the shell 108. In an embodiment, the cold pack may be embedded within the walls of the shell 102 and/or the shell 108. In an embodiment the cold pack may be in the form of a gel, may include materials known in the art. In an embodiment, the gel packs may include hydroxyethyl cellulose, or sodium polyacrylate, or vinyl coated silica gel, or any other suitable material well known in the art. It may be appreciated the cold packs may be refrigerated before positioning the cold packs in the mouth of the patient. Alternatively, the thermal pack 150 may be a hot pack to provide heat to the teeth 106 and accelerates a movement of the teeth by increasing blood flow in regions around the teeth 106. In an embodiment, the hot pack may be microwavable and is filled with a material having a specific heat capacity in a predetermined specific heat capacity range. In an embodiment the hot pack may include a material, such as, wheat, buckwheat, flax seed, rice, etc., and is covered by insulative material. In an embodiment, the hot pack may include an aromatic material, such as, but not limited to, essential oils, cloves cinnamon, mint, or any other similar material known in the art. In an embodiment, the inner shell 102 may have a window/cut-out to allow a more direct contact of the heat pack or cold pack with the teeth 106. In an embodiment, the cold pack and the hot pack are alternatively used to accelerate tooth movement or can be attached at different locations simultaneously. The thermal pack 150 may be inserted in a package that is impervious to saliva to prevent a seepage of saliva into the thermal pack 150. An activation of the hot pack may be performed by using an exothermic reaction, or by heating using microwave. In an embodiment, the hot pack may be suitable for a single use and may generate heat as a result of exothermic chemical reaction. In an embodiment, the heat may be generated due to an exothermic chemical reaction of moist iron powder and salt, or due enthalpy change of a solution of calcium chloride. In an embodiment the hot pack may be reusable packs, and may contain a supersaturated solution of sodium acetate in water. Although the supersaturated solution of sodium acetate in water is contemplated, it may be envisioned that the other suitable materials, such as, but not limited to, magnesium sulfate, calcium chloride, etc., whose crystallization is triggered by flexing flat ferrous metal embedded in the liquid can also be utilized. The shell 102 or the shell 104 may also include a sensor that may provide information about a temperature of the shell 102 or the shell 104 to prevent possible tissue burns.

Figure 7:
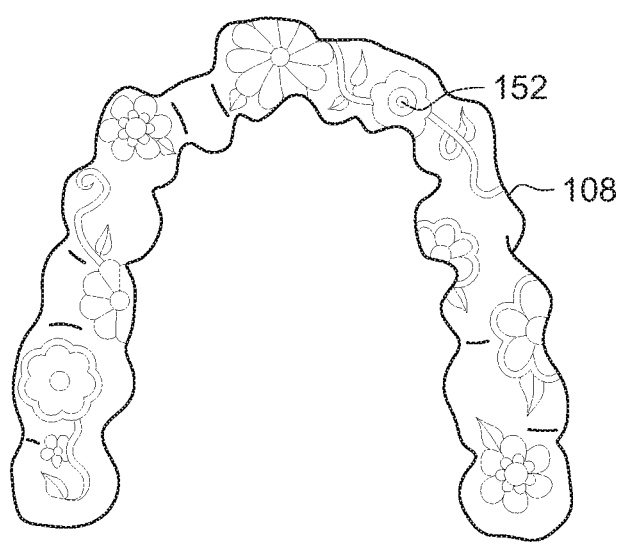
FIG. 7 illustrates a shell having various designs, in accordance with an embodiment of the present invention.

Further, in an embodiment, as shown in FIG. 7, the outer shell 108 may include various colors, designs motifs 152 such as, images of flowers, or coatings, etc., to make the visible outer shell 108 aesthetically appealing by using methods well known by those skilled in the art. The images may be etched or printed on the outer shell 108 by methods well known by those skilled in the art. The design may be formed on the outer shell 108 by using one or more digital printing or any other technique known in the art. Further, designs 152 may be formed using different colors and materials. In an embodiment, the material used for forming designs 152 on the outer shell 108 may include one or more flavoring agents, such as, but not limited to, mint, cinnamon, etc. In an embodiment, one or more fang structures may be added to the outer shell 108. In this manner the shell 108 may be individualized and changed from one shell to another shell during a course of the treatment.

Figure 8A:
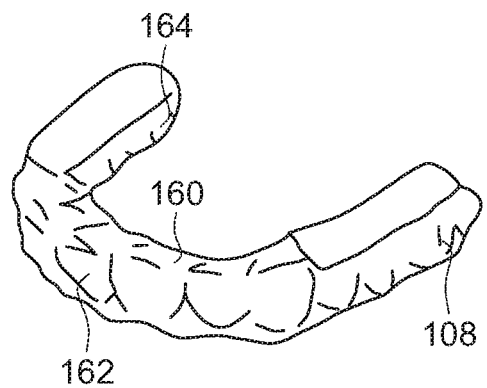
FIG. 8A illustrates a shell having a portion of an outer surface as a flat surface, in accordance with an embodiment of the present invention.
Figure 8B:
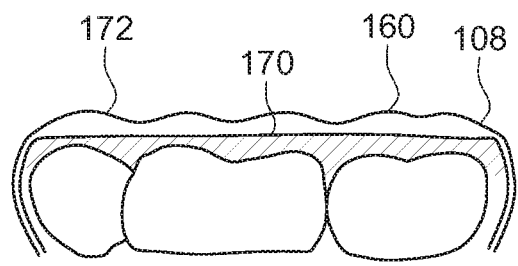
FIG. 8B illustrates a shell having a portion of an inner surface as a flat surface, in accordance with an embodiment of the present invention.
Figure 8C:
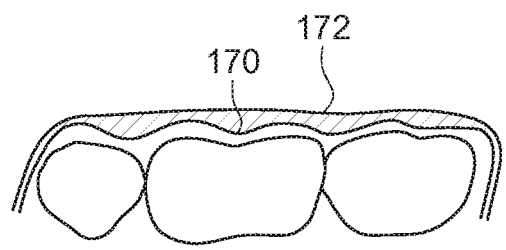
FIG. 8C illustrates a sectional view of the shell of FIG. 8A, in accordance with an embodiment of the present invention.

In an embodiment, as shown in FIGS. 8A, 8B, and 8C, the outer shell 108 includes a base wall 160 connecting a front wall 162 and a rear wall 164 of the outer shell 108. The base wall 160 includes an inner surface 170 and an outer surface 172 that contacts the opposing teeth and may be referred as biting surface 160. In certain embodiment, at least a portion of the inner surface 170 may be a flat surface (as shown in FIG. 8B). In certain other embodiments, at least a portion of the outer surface 170 may be a flat surface and the inner surface may be a non-tooth contacting (as shown in FIGS. 8A and 8C). The flat surfaces 170, 172 facilitates tooth movement without the tooth catching on the inner wall of the shell 108. Furthermore, due to a presence of a relief between the teeth and the base wall 160, the biting forces are not transmitted to the teeth, thereby minimizing direct intrusive forces to the teeth Also, the flat surface 172 facilitates sliding of one jaw against the other jaw and thereby prevent locking of the upper jaw and the lower jaw and its repositioning.

Figure 8D:
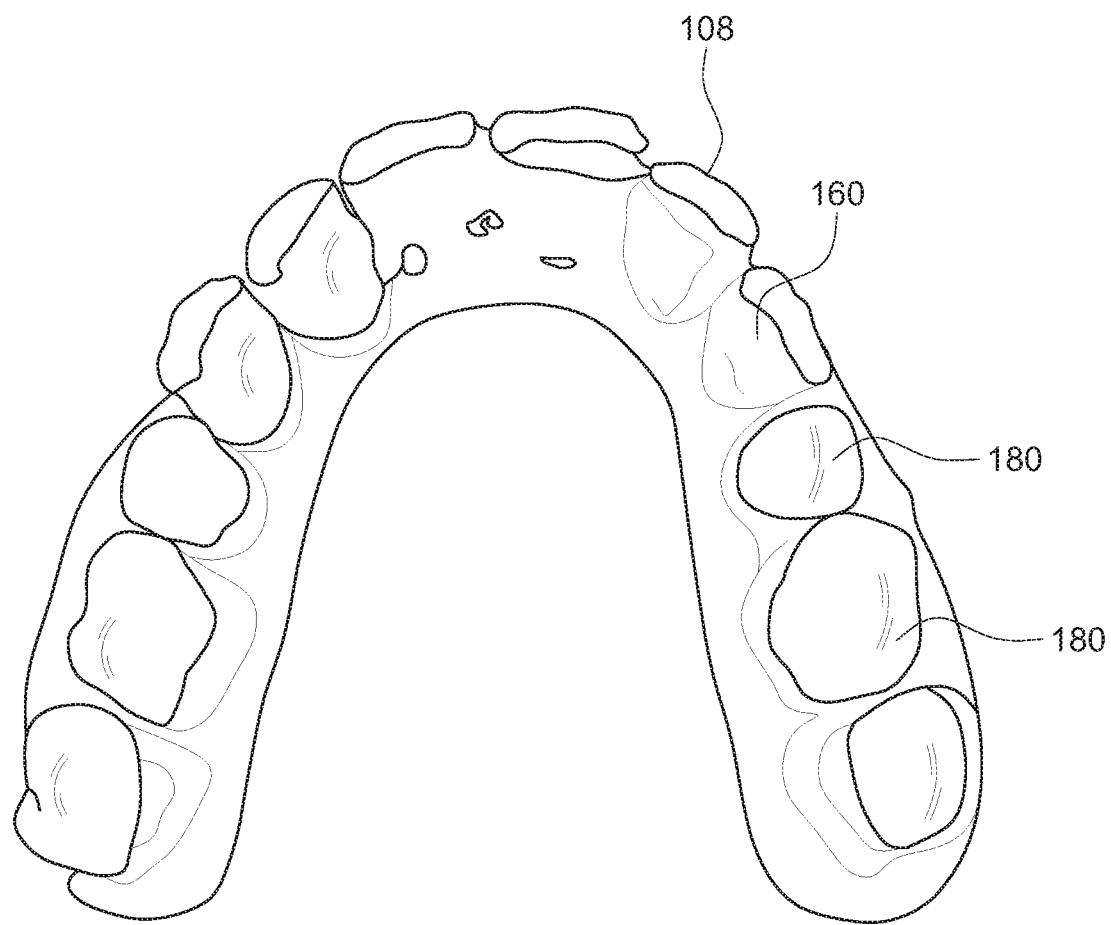
FIG. 8D illustrates a shell having one or more cut-outs, in accordance with an embodiment of the present invention.

In some embodiments, the base wall 160 that is the wall that faces the biting surfaces of the teeth may include one or more cut outs 180 (as shown in FIG. 8D) extending from the outer surface 172 to the inner surface 170. In this manner, biting surfaces of the teeth corresponding to the cut-outs 180 are open to directly contact opposing teeth. By eliminating the intervening layer of the shell 108 that is parts of the base 160, the wearing down and breakage of the shells 108 due to the biting forces is minimized. Although, the flat surfaces are contemplated for the outer shell 108, it may be appreciated that the inner shell 102 may include similar flat surfaces and/or cut-outs. Although, the flat surfaces and cut-outs are explained with reference an aligner assembly having two shells, it may be appreciated that the cut-outs and flat surfaces may be included in any aligner assembly having a single shell or more than two shells. Further, one or more components of the aligner assembly may made of bio-degradable material known in the art. In an embodiment, the bio-degradable material may be composed of a range of bio fillers, natural and synthetic biodegradable polymers, or elastomers. In an embodiment, the bio-degradable material that are used may be the materials certified according to ASTM D6400 or EN 13432. In an example, a flexural modulus of the biodegradable material may be in a range of 25 million pounds per square inch to 45 million pounds per square inch. In an example, a hardness the biodegradable material may be in a range of 50A to 100D. In an embodiment, surfaces of the one or more components made from biodegradable material may be coated with polymers using simple techniques such as dip-coating, spray-coating, spin-coating, or solvent casting. Coating techniques involving the chemical grafting of molecules onto the biomaterial surface may also be utilized. Nano-thin coatings based on self-assembled monolayers (SAMs), surface-tethered polymers (polymer brushes), or multilayer coatings based on layer-by-layer assembly that offer precise control on the location and orientation of chemical groups and biomolecules on the surface of the coating may also be utilized.

Figure 9A:
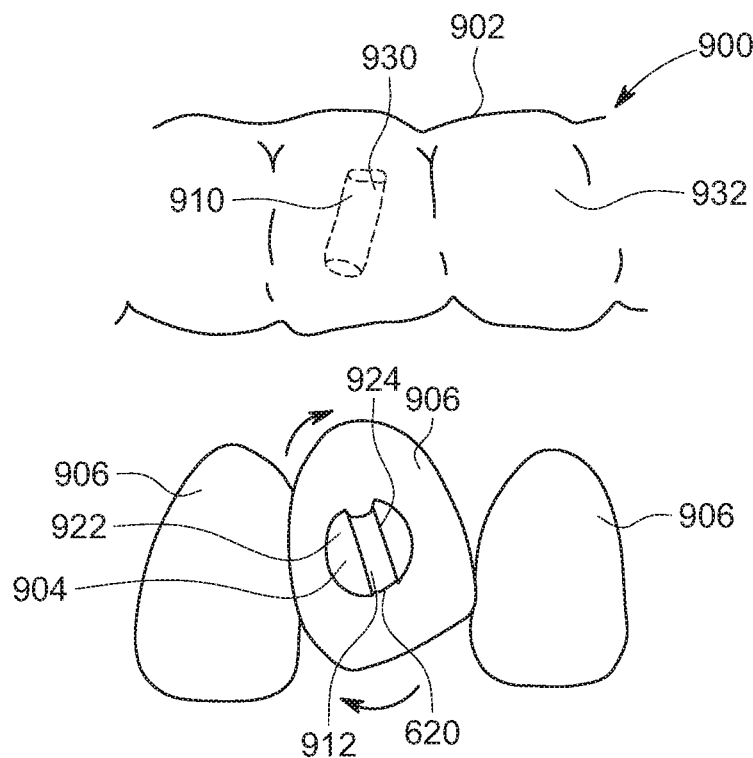
FIG. 9A illustrates an aligner assembly having a shell and an engagement structure attached to one or more teeth, in accordance with an embodiment of the present invention.
Figure 9B:
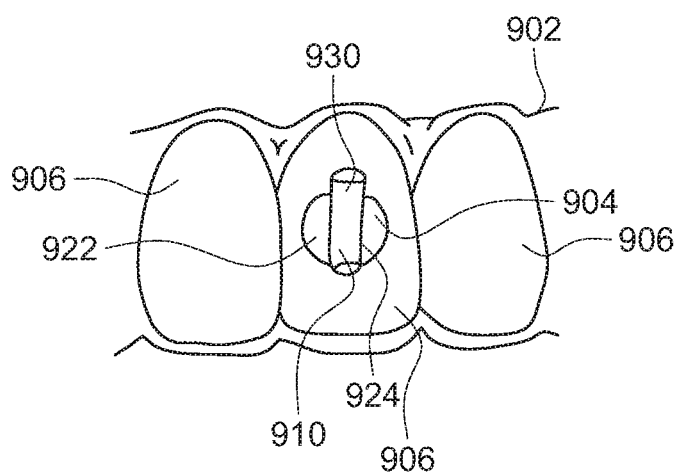
FIG. 9B illustrates the aligner assembly of FIG. 9A depicting an engagement of a cooperating structure of the aligner assembly with the engagement structure, in accordance with an embodiment of the present invention.

Referring to FIGS. 9A, and 9B, an aligner assembly 900 is shown according to an alternative embodiment of the disclosure. The aligner assembly 900 is different from the aligner assembly 100 in the aspect that the aligner assembly 900 include only an outer shell 902 (hereinafter referred to as shell 902) and the inner shell 102 of the aligner assembly 100 is omitted. Further, one or more engagement structures 904 of the aligner assembly 900 are directly attached to teeth 906 of the patient. The aligner assembly 900 may include the shell 902 and the one or more engagement structures 904 attached to the one or more teeth 906. The shell 906 includes a plurality of cavities for receiving a plurality of teeth such that each cavity is adapted to receive only a single tooth of the plurality of teeth 906. Further, the shell 902 may include one or more cooperating structures 910 disposed on an inner surface of the shell 902 and adapted to engage with one or more engagement structures 904 to exert a force and/or torque on one or more teeth 906 to facilitate a repositioning of the teeth. Further, each engagement structure 904 may include a slot 912 to receive a portion of the cooperating structure 910. As shown, the engagement structure 904 may include a base 920, a first wall 922 extending outwardly from the base 920, and a second wall 924 disposed space apart from the first wall 922 and defining the slot 912 therebetween. The base 920 is adapted to be attached to a surface of the tooth 906. In an embodiment, the base 920 may be removably attached to the surface of the tooth 906 through an intermediary attachment (not shown) bonded on the tooth 906). In an embodiment, the base 920 may be attached to the tooth using a dental bonding agent. In an embodiment, the base 920 may be omitted, and in such a case, the first wall 922 and the second wall 924 may be directly attached to the tooth 906.

Further, as shown, the cooperating structure 910 may be a lip 930 extending inside the cavity from an inner surface of the shell 902. In an embodiment, the lip 930 may be disposed at an inner surface of a front wall 932 of the shell 902. The lip 930 is adapted to be inserted into the slot 912 of the engagement structure 904, and may apply a force and/or torque on the tooth 906 to facilitate a partial or a complete repositioning of the tooth 906. In an embodiment, a relative orientation of the slot 912 and the lip 930 may be selected based on a desired amount of force and/or torque to be applied on the tooth 906 and/or a desired line of action of force and/or torque on the tooth 906 and/or a desired point of application of force and/or a desired direction of force to achieve a desired tooth movement. In an embodiment, the lip 930 may be integrally formed with the shell 902 or may be removably attached to the inner surface of the shell 902. In an embodiment, the lip 930 may be made of a material which is different from a material of the shell 902. In an embodiment, the lip 930 may be made of a shape memory alloy or a fiber reinforced composite. However, it may be envisioned that the lip 930 can made of any material suitable for use in a mouth of a patient. In an embodiment, a stiffness and/or rigidity of the lip 930 may be different from a stiffness and/or rigidity of the rest of the shell 902. The aligner assembly 900 is adapted to provide effective and efficient delivery of forces, and hence reduces the total number of changes shell 902 for repositioning one or more teeth 906 from the initial position to the final position. Further, in a case, where the cooperating structure 910 is removably attached to the shell 902 or is made of the shape memory alloy, the teeth 906 may be repositioned from the initial position to the final position without changing the shell 902. Further, in an embodiment, the engagement structures 904 may be formed or attached to the inner surface of the shell 902. In such a case, the cooperating structures 910 may be attached or bonded to the tooth. Although, the embodiment discussed in FIGS. 4-8 are discussed with the inner shell 102 and/or the outer shell 108, it may be appreciated that embodiments may be applied to any of the shells 102, 108. Also, the embodiments discussed in FIGS. 4-8 may applied to an aligner assembly having a single shell.

Figure 10A:
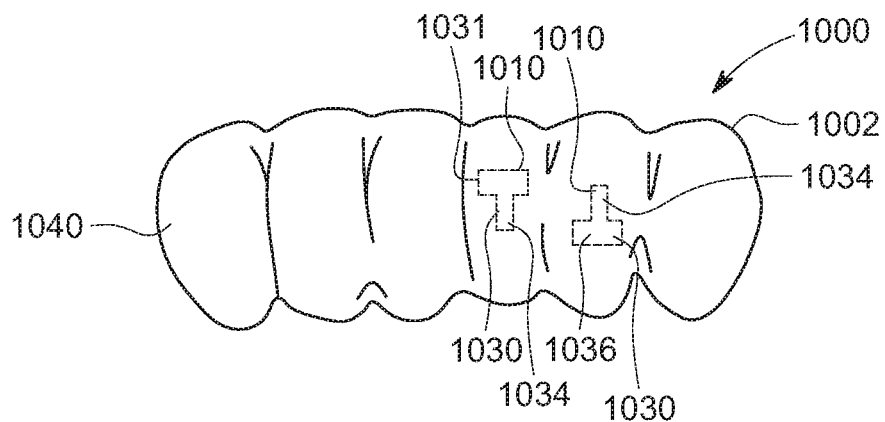
FIG. 10A illustrates an aligner assembly having a shell having one or more cooperating structure, in accordance with an embodiment of the present invention.
Figure 10B:
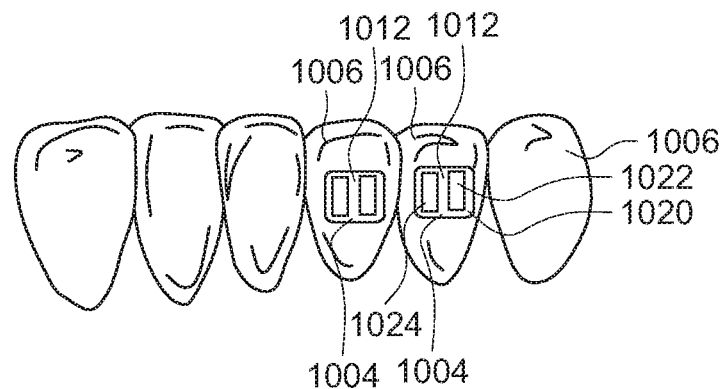
FIG. 10B illustrates one or more engagement structures of the aligner assembly of FIG. 10A attached to one or more teeth, in accordance with an embodiment of the present invention.

Referring to FIGS. 10A and 10B, another exemplary aligner assembly 1000 is shown. The aligner assembly 1000 is similar to the aligner assembly 900 except in structure of engagement structures and cooperating structure. The aligner assembly 1000 includes a shell 1002, one or more engagement structures 1004 attached to the one or more teeth 1006. The shell 1002 includes one or more cavities for receiving the one or more teeth 1006 such that each cavity is adapted to receive only a single tooth of the one or more teeth 1006. Further, the shell 1002 may include one or more cooperating structures 1010 disposed on an inner surface of the shell 1002 and adapted to engage with one or more engagement structures 1004 to exert a force and/or torque on one or more teeth 1006 to facilitate a repositioning of the teeth 1006. Further, each engagement structure 1004 may include a slot 1012 to receive a portion of the cooperating structure 1010. As shown, the engagement structure 1004 may include a base 1020, a first wall 1022 extending outwardly from the base 1020 and a second wall 1022 disposed space apart from the first wall 1020 and defining the slot 1020 therebetween. The base 1020 is adapted to be attached to surface of the tooth 1006. In an embodiment, the base 1020 may be removably attached to the surface of the tooth 1006. In an embodiment, the base 1020 may be attached to the tooth using a dental bonding agent, or any other means known in the art.

Further, as shown, the cooperating structure 1010 may be T-shaped 1030 or inverted T-shaped structure extending inside the cavity from an inner surface of the shell 1002. The cooperating structure 1010 may include a first elongated member 1034 and a second elongated member 1036 extending substantially perpendicular to the first elongated member 1034 and contacting a first end of the first elongated member 1034. The second elongated member 1036 may extend on both sides of the first elongated member 1034. In an embodiment, the cooperating structure 1010 may be disposed at a front wall 1040 of the shell 1002. The cooperating structure 1010 may be adapted to engage with the engagement structure 1004 such that the first elongated member 1034 is, at least partly, received with the slot 1012 and the second elongated member 1036 may contact the first wall 1022 and/or the second wall 1024 to apply a force and/or torque on the tooth 1006 to facilitate a partial or a complete repositioning of the tooth 1006. In an embodiment, the second elongated member 1036 may rest or abut against the top end of the first wall 1022 and the second wall 1024 to push the tooth in a downward direction to facilitate an intrusion of the tooth 1006. In another embodiment, the second elongated member 1036 may abut against the bottom end of the first wall 1022 and the second wall 1024 to apply a push force on the tooth 1006 in an upward direction to facilitate extrusion of the tooth 1006. It may be envisioned that, a relative orientation of the slot 1012 and first elongated member 1024 and/or the second elongated member 1026 may be selected based on a desired amount of force and/or torque to be applied on the tooth 1006 and/or a desired line of action of force and/or torque on the tooth 1006 and/or a desired point of application of force and/or a desired direction of force to achieve a desired tooth movement. Sizes, dimensions, and inclinations or orientations of the cooperating structures 1010 and/or the engagement structures 1004 is incrementally changed during the course of treatment to move the one or more teeth 1006 form the initial position to the final position.

Figure 11A:
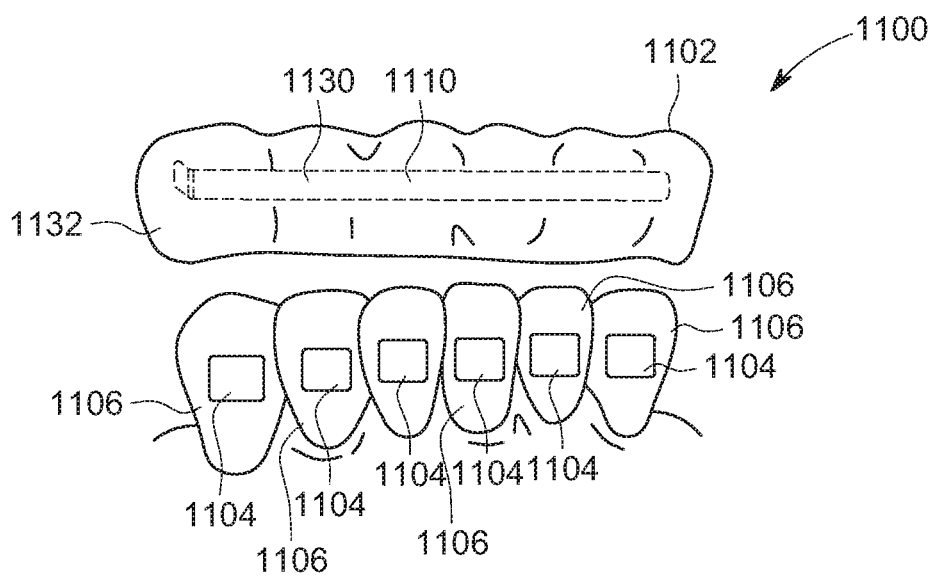
FIG. 11A illustrates an aligner assembly having a shell having a cooperating structure, in accordance with an embodiment of the present invention.
Figure 11B:
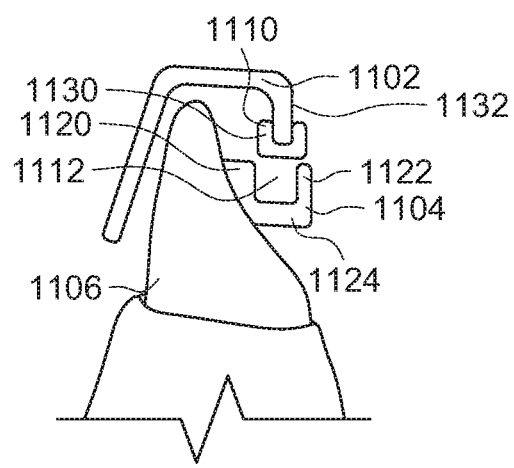
FIG. 11B illustrates a side view of the aligner assembly of FIG. 11A depicting an engagement of an engagement structure with the cooperating structure, in accordance with an embodiment of the present invention.
Figure 11C:
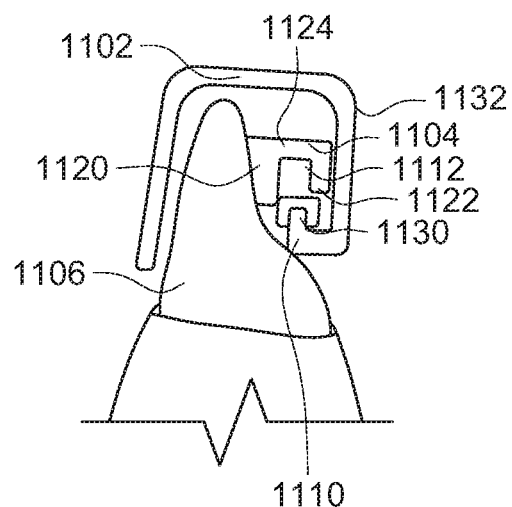
FIG. 11C illustrates a side view of the aligner assembly of FIG. 11A depicting an engagement of an engagement structure with the cooperating structure, in accordance with an embodiment of the present invention.

Referring to FIGS. 11A, 11B, and 11C another exemplary aligner assembly 1100 is shown. The aligner assembly 1100 is similar to the aligner assembly 900 except in structure of engagement structures and cooperating structures. The aligner assembly 1110 may include a shell 1102 and one or more engagement structures 1104 attached to the one or more teeth 1106. The shell 1102 includes one or more cavities for receiving one or more teeth 1106 such that each cavity is adapted to receive only a single tooth of the one or more teeth 1106. Further, the shell 1102 may include a single cooperating structure 1110 disposed on an inner surface of the shell 1102 and adapted to engage with all the engagement structures 1104 to exert a force and/or torque on the teeth 1106 to facilitate a repositioning of the teeth 1106. In an embodiment, the cooperating structure 1110 may be removably attached to the shell 1102. By incrementally changing the size and a dimension of the cooperating structure 1110 without changing the shell 1102, incremental repositioning the teeth 1106 from an initial position to a final position may be facilitated. In an embodiment, the cooperating structure 1110 may be snap fitted or held with pressure sensitive adhesive or bonded to the shell 1102. Also, the cooperating structure 1110 can be formed by incrementally adding a material. Further, each engagement structure 1104 may include a slot 1112 to receive a portion of the cooperating structure 1110. As shown, the engagement structure 1104 may include a first wall 1120 adapted to be attached to surface of the tooth 1106, a second wall 1122 disposed spaced apart from the first wall 1120 and defining the slot 1112 therebetween. Further, the engagement structure 1104 may include an arm 1124 extending substantially perpendicularly to the tooth 1106 and connecting the first wall 1120 to the second wall 1122. In an embodiment, as shown in FIG. 11B, shows the aligner assembly 1100 designed for the lower teeth having the engagement structure 1104 that may be coupled to the tooth 1106 such that the arm 1124 defines a base of the engagement structure 1104 and slot 1112 is open at top to facilitate an intrusion of the lower teeth. Alternatively, as shown in FIG. 11C, the engagement structure 1104 may be coupled to the tooth 1106 such that arm 1124 defines a roof of the engagement structure 1104 and the slot 1112 is open at the bottom. In an embodiment, the first wall 1120 may be removably attached to the surface of the tooth 1106. It may be envisioned that an orientation of the slot 1112 may be selected based on a desired amount of force and/or torque to be applied on the tooth 1106 and/or a desired line of action of force and/or torque on the tooth 1106 and/or a desired point of application of force and/or a desired direction of force to achieve a desired tooth movement. In an embodiment, the first wall may be attached to the tooth 1106 using a dental bonding agent, by threading or any other means known in the art. Further, it may be appreciated that the one or more components of the aligner assembly 1100 may be made of any suitable material known in the art. Also, a thickness of any portion of one or more components may be changed/varied to change a stiffness that portion of the component. Also, sizes, dimensions, and inclinations or orientations of the cooperating structures 1110 and/or the engagement structures 1104 is incrementally changed during the course of treatment to move the one or more teeth form the initial position to the final position.

Figure 11D:
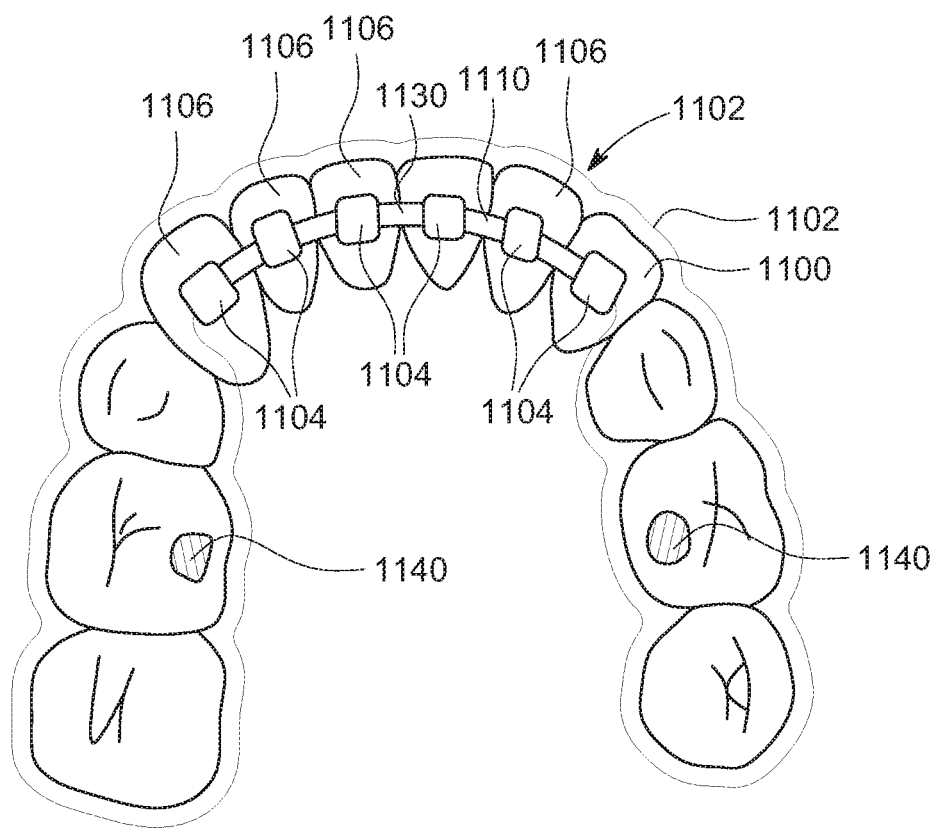
FIG. 11D illustrates a top view of the aligner assembly of FIG. 11A, in accordance with an embodiment of the present invention.

Further, as shown, the cooperating structure 1110 may be an elongated shaft 1130 extending along a width of the shell 1102 may extend inside the cavities from an inner surface of the shell 1102. In an embodiment, the cooperating structure 1110 may be disposed at a front wall 1132 of the shell 1102. The cooperating structure 1110 may be adapted to engage with the engagement structures 1104 such that the elongated shaft 1130 is, at least partly, received inside the slots 1112 of the engagement structures 1104 to apply a force and/or torque on the teeth 1106 to facilitate a partial or a complete repositioning of the teeth 1106. Further, as shown in FIG. 11D, the aligner assembly 1110 may include one or more passive retention/stabilization members 1140 to facilitate a retention of the shell 1102 with the teeth 1106 and prevent the shell 1102 from slipping out in response to the opposing reactive forces.

Figure 12A:
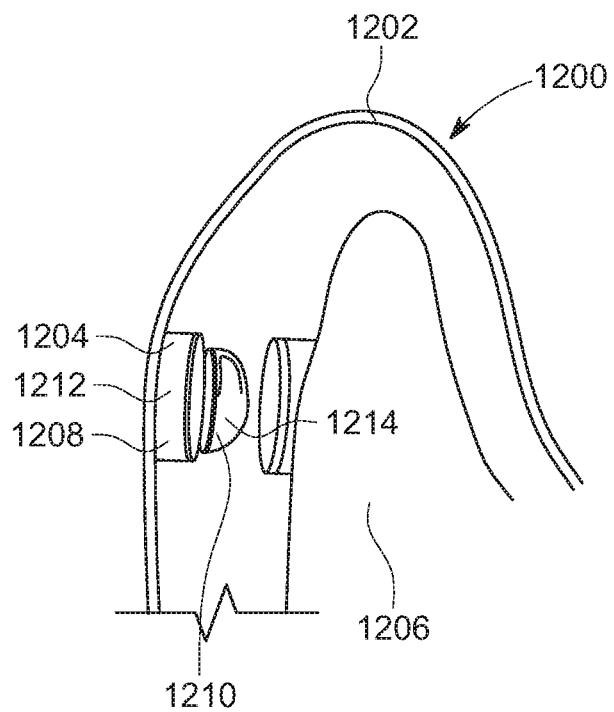
FIG. 12A illustrates a sectional view of an aligner assembly depicting an engagement structure having a first member and a second member removably coupled to the first member, in accordance with an embodiment of the present invention.
Figure 12B:
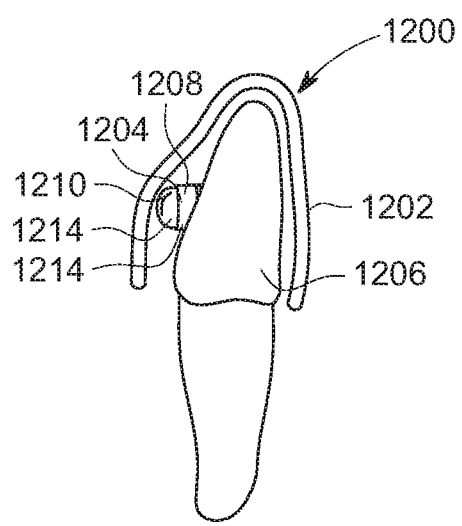
FIG. 12B illustrates a sectional view of an aligner assembly depicting an engagement structure having a first member and a second member removably coupled to the first member, in accordance with an embodiment of the present invention.

Referring to FIGS. 12A to 15B, various aligner assemblies shown according to an alternative embodiment of the disclosure. Referring to the FIGS. 12A, and 12B, an exemplary aligner assembly 1200 is shown. The aligner assembly 1200 may include a shell 1202 having one or more cavities adapted to receive one or more teeth 1206, and one of more engagement structures 1204 adapted to engage with the shell 1202 and the teeth 1206 to facilitate a repositioning of teeth 1206 to an intermediate position or a final position. As shown, the engagement structure 1204 may include a first member 1208 and a second member 1210 retentively/removably coupled/engaged with the first member 1208. It may be appreciated that the second member 1210 may be attached/engaged with the first member 1208 by using snap fit arrangement, or a threads, or adhesive, or by any other means, known in the art, that facilitates an easy removal and engagement of the second member 1210 to the first member 1208. As illustrated, the first member 1208 may be a hollow hemispherical member 1212 and the second member 1210 may be a bubble shaped member 1214 configured to engaged with the hollow hemispherical member 1212. The second member 1210 is adapted to protrude outwardly when in engagement with the hemispherical member 1212. It may be appreciated that a size and shape of the second member 1210 (i.e. the bubble shaped member 1214) may be changed to apply force or torque on the tooth 1206 to reposition the tooth from one position to each subsequent position. In an embodiment, as shown in FIG. 12A, the first member 1208 may be attached or integrally formed to an inner surface of the shell 1202. Alternatively, as shown in FIG. 12B, the first member 1208 may be attached/coupled to the tooth by using various means known in the art. In an embodiment, the bubble shaped member 1214 may be adhesively attached to the shell 1202 or the one or more teeth 1206 by using a two way adhesive tape. In such a case, the first member 1208 (i.e. the hollow hemispherical member 1212) may be omitted. Although the first member 1208 is contemplated as the hollow spherical member 1212, it may be envisioned that the first member 1208 may include any shape that facilitates an attachment of the bubble shaped member 1214 to the shell 1202 or the tooth 1206. Further, in some embodiments, the bubble shaped member 1214 be a hollow member that can be filled with one or more substances, such as, but not limited to, compressed air, gel, or elastomeric composite, etc., to incrementally vary a size of the bubble shaped member 1214 and create different forces during the course of treatment. In this manner, there is no need to change the second member 1210 to incrementally move the one or more teeth 1206 from an initial position to a final position.

Figure 13:
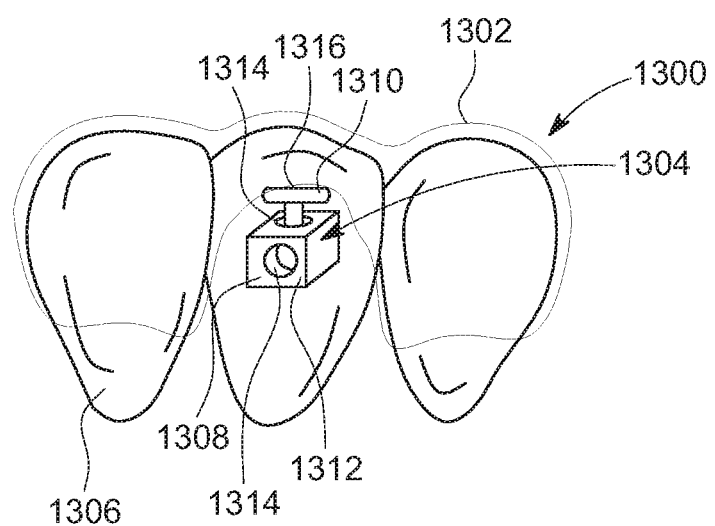
FIG. 13 illustrates a sectional view of an aligner assembly depicting an engagement structure having a first member and a second member removably coupled to the first member, in accordance with an embodiment of the present invention.

Referring to the FIG. 13, another exemplary aligner assembly 1300 is shown. The aligner assembly 1300 may include a shell 1302 having one or more cavities adapted to receive one or more teeth 1306, and one of more engagement structures 1304 adapted to engage with the shell 1302 and the teeth 1306 to facilitate a repositioning of the one or more teeth 1306 to an intermediate position or a final position. As shown, the engagement structure 1304 may include a first member 1308 and a second member 1310 retentively/removably coupled/engaged with the first member 1308. It may be appreciated that the second member 1310 may be attached to the first member 1308 by using snap fit arrangement, or a threads, or adhesive, or by any other means, known in the art, that facilitates an easy removal and engagement of the second member 1310 to the first member 1308. As illustrated, the first member 1308 may be a cuboidal structure 1312 having a hole 1314 on each surface, and the second member 1310 may be a nail shaped member 1316 configured to received partly within the hole 1314 of the cuboidal structure 1312. Further, the first member 1308 may be attached/coupled to the tooth 1306 by using various means known in the art. A force may be applied on the second member 1310 by the shell 1302, which in turn applies force on the tooth 1306 via the first member 1308 to facilitate repositioning of the tooth 1306. In an embodiment, the nail shaped member 1310 may be rotated to increase a height of the nail shaped member that is disposed above the hole, thereby creating forces to move the tooth 1306.

Figure 14A:
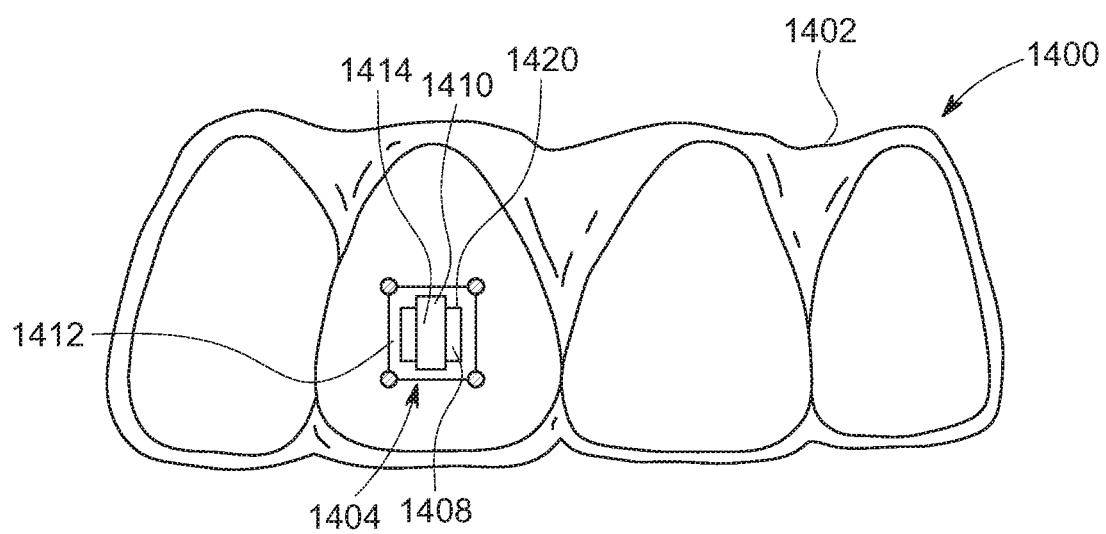
FIG. 14A illustrates an aligner assembly depicting an engagement structure having a first member and a second member removably coupled to the first member, in accordance with an embodiment of the present invention.
Figure 14B:
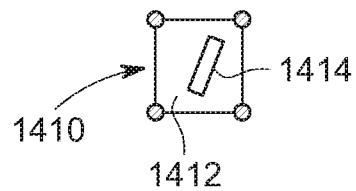
FIG. 14B illustrates the second member of the engagement structure of FIG. 14A, in accordance with an embodiment of the present invention.
Figure 14C:
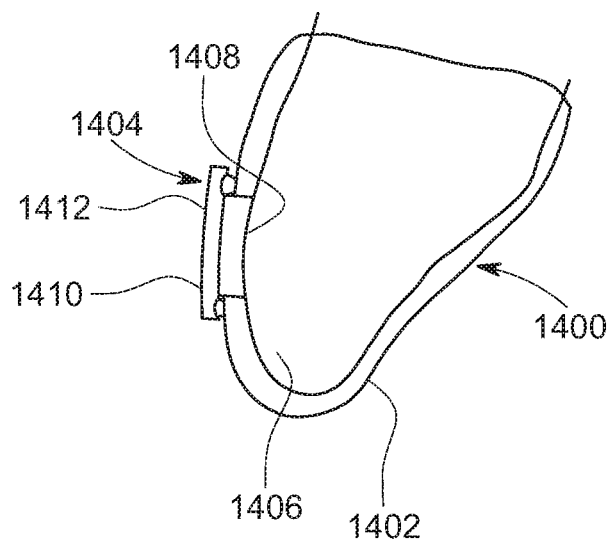
FIG. 14C illustrates a sectional view of the aligner assembly depicting the engagement structure having the first member and the second member removably coupled to the first member, in accordance with an embodiment of the present invention.

Referring to the FIGS. 14A, 14B and 14, another exemplary aligner assembly 1400 is shown. The aligner assembly 1400 may include a shell 1402 having one or more cavities adapted to receive one or more teeth 1406, and one of more engagement structures 1404 adapted to engage with the shell 1402 and the teeth 1406 to facilitate a repositioning of the teeth 1406 to an intermediate position or a final position. As shown, the engagement structure 1404 may include a first member 1408 and a second member 1410 retentively/removably coupled/engaged with the first member 1408. As illustrated, the second member 1410 includes a rectangular plate 1412 and an elongated lip 1414 in shape of a protrusion extending outwardly from the plate 1412. The plate 1412 may be adhesively attached to the shell 1402 by applying adhesive on various corners of the base or along edges of the plate 1412. The plate 1412 is adhesively attached to the shell 1402 such that the lip 1414 may extend inside the cavity of the shell 1402 through a cut-out in the shell 1412. Further, the first member 1408 may include a base, a first wall extending outwardly from the base, and a second wall disposed space apart from the first wall and defining a slot 1420 therebetween. The first member 1408 is adapted to be attached to surface of the tooth 1406. In an embodiment, the first member 1408 may be attached to the tooth using a dental bonding agent, by threading or any other means known in the art. The lip 1414 is adapted to be inserted into the slot 1420 of the first member 1408 and may apply a force and/or torque on the tooth 1406 to facilitate a partial or a complete repositioning of the tooth 1406. In an embodiment, a relative orientation of the slot 1420 and the lip 1414 may be selected based on a desired amount of force and/or torque to be applied on the tooth 1406 and/or a desired line of action of force and/or torque on the tooth 1406 and/or a desired point of application of force and/or a desired direction of force to achieve a desired tooth movement. As the second member 1410 can be removed, the second member 1410 of different sizes may be utilized over the entire treatment of the patient to reposition the teeth from an initial position to the final position via various intermediate positions. Also lip 1414 may be made of different materials having varied stiffness.

Figure 15A:
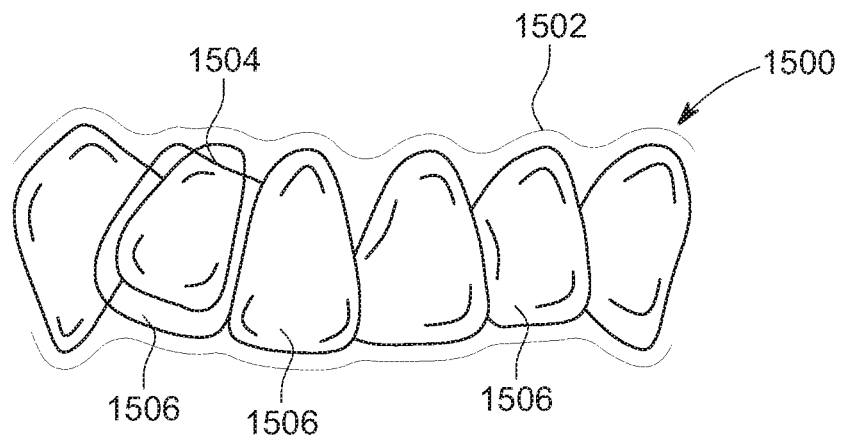
FIG. 15A illustrates an aligner assembly depicting an engagement structure having a first member and a second member removably coupled to the first member, in accordance with an embodiment of the present invention.
Figure 15B:
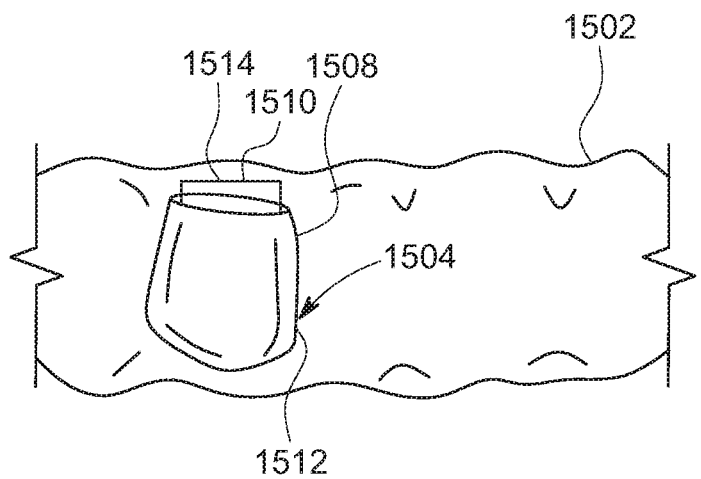
FIG. 15B illustrates a sectional view of the aligner assembly depicting the engagement structure having the first member and the second member removably coupled to the first member, in accordance with an embodiment of the present invention.
Figure 15C:
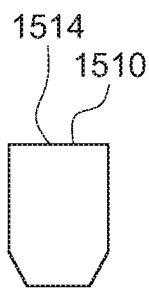
FIG. 15C illustrates the second member of the engagement structure, in accordance with an embodiment of the present invention.

Referring to the FIGS. 15A, 15B, and 15C, another aligner assembly 1500 is shown. The aligner assembly 1500 may include a shell 1502 having one or more cavities adapted to receive one or more teeth 1506, and one of more engagement structures 1504 adapted to engage with the shell 1502 and the teeth 1506 to facilitate a repositioning of teeth 1506 to an intermediate position or a final position. As shown, the engagement structure 1504 may include a first member 1508 and a second member 1510 retentively/removably coupled/engaged with the first member 1508. As illustrated, the first member 1508 may be a pocket 1512 formed on an inner surface of the shell 1502, while the second member 1510 may be a shim 1514 configured to be inserted inside the pocket 1512. It may be appreciated that a thickness of the shim 1514 (the second member 1510) is changed to apply force or torque on the tooth 1506 to reposition the tooth 1506 from one position to each subsequent position. For changing the thickness of the shim 1514, a plurality of shims may be inserted inside the pocket 1512. In addition, a thickness of a single shim 1514 maybe increased by incrementally building material over the shim 1514.

Figure 16A:
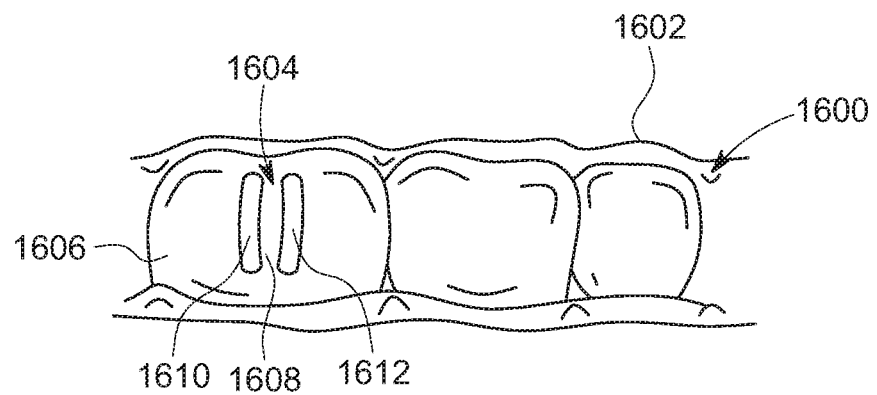
FIG. 16A illustrates an aligner assembly having strip formed by a pair of slits, in accordance with an embodiment of the present invention.
Figure 16B:
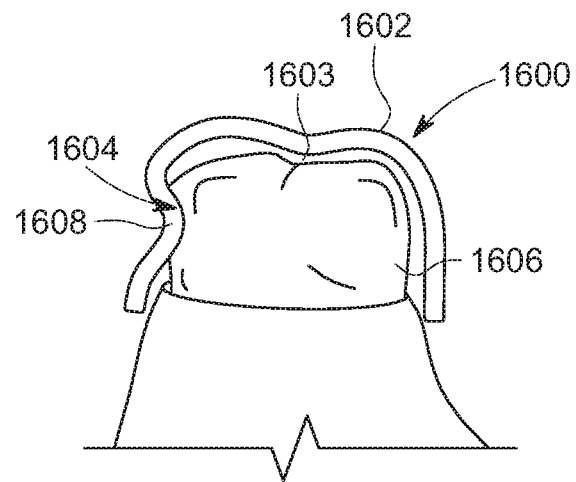
FIG. 16B illustrates a sectional view of the aligner assembly, in accordance with an embodiment of the present invention.

Referring to FIGS. 16A and 16B, an aligner assembly 1600 according to an alternative embodiment of the disclosure is shown. The aligner assembly 1600 includes a shell 1602 having one or more cavities 1603 adapted to receive a one or more teeth 1606, and one of more engagement structures 1604 adapted to engage the one or more teeth 1606 to facilitate repositioning of the tooth 1606 to an intermediate position or a final position. As shown, the engagement structure 1604 may include a strip 1608 formed by cutting a pair of slits 1610, 1612 in the shell 1602. In an embodiment, the shell 1602 may be pre-contoured along the strip 1608 and the slits 1610, 1612 may add flexibility of the strip 1608 to selectively increase the extension of the strip 1610 inwardly towards tooth 1606. The strip 1608 deforms to engage the tooth 1606 and as result generates a force on the tooth 1606 to reposition the tooth 1606. Also, the strip 1608 may be created in any direction depending on a desired line of action of force and/or a desired point of application of force, a desired direction of force, or a desired amount of force. In an embodiment, a pre-shaped strip 1608 may be affixed to the shell 1602 and may include a shape memory alloy to increase a working range of the aligner assembly 1600. In an embodiment, the slit 1608 may include a material different from material of the rest of shell 1602. In an implementation, a stiffness of the strip 1608 can be changed by varying a width, thickness, or any other dimension of the strip 1608, or by using a material different from the rest of the shell 1602. In an embodiment, the multiple strips can be formed into shell 1602. Further, an orientation of the strip 1608 and the slits 1610, 1612 may be selected based on a desired point of application of force and/or a desired direction of force and/or a desired line of action of force. Further, it may be appreciated that additional attachment, such as a bubble, may be attached to the strip 1608 to enhance a force applied by the strip 1608 on the tooth 1606. In embodiment, the strip 1608 may be thermo-mechanically deformed to increase a convexity of the strip 1608.

Figure 17:
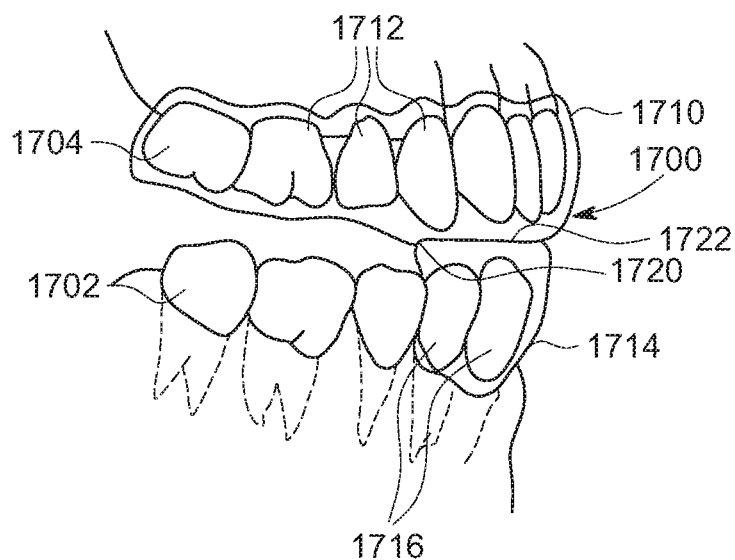
FIG. 17 illustrates an aligner assembly having a first shell and a second shell, in accordance with an embodiment of the present invention.

Referring to FIG. 17, an aligner assembly 1700 according to an alternative embodiment of the disclosure is shown. The aligner assembly 1700 is configured to facilitate a relative movement between a lower jaw 1702 and an upper jaw 1704 to hold the lower jaw 1702 forward with respect to the upper jaw 1704. As shown, the aligner assembly 1700 may include a first shell 1710 configured to receive one or more teeth 1712 of an upper jaw 1704, and a second shell 1714 adapted to receive one or more teeth 1716 of the lower jaw 1702. As shown, the first shell 1710 is attached with the second shell 1714. In an embodiment, an upper wall 1720 of the first shell 1710 is attached to an upper wall 1722 of the second shell 1744 to create a unified structure. In an embodiment, the first shell 1710 and the second shell 1714 are integrally formed with each other. The first shell 1710 may extend along an entire length of the upper jaw 1704 or only a segmented of the upper jaw 1704. Similarly, the second shell 1714 may extend along an entire length of the lower jaw 1702 or only a segmented of the lower jaw 1702. The illustrated aligner assembly 1700 is configured to hold the lower jaw forward against the upper jaw 1702 to facilitate alignment of the lower jaw 1702 with the upper jaw 1704. Further, it may be appreciated that when the aligner assembly 1700 is worn by the patient, the lower law 1702 needs to be positioned forward relative to the upper jaw 1704.

Figure 18:
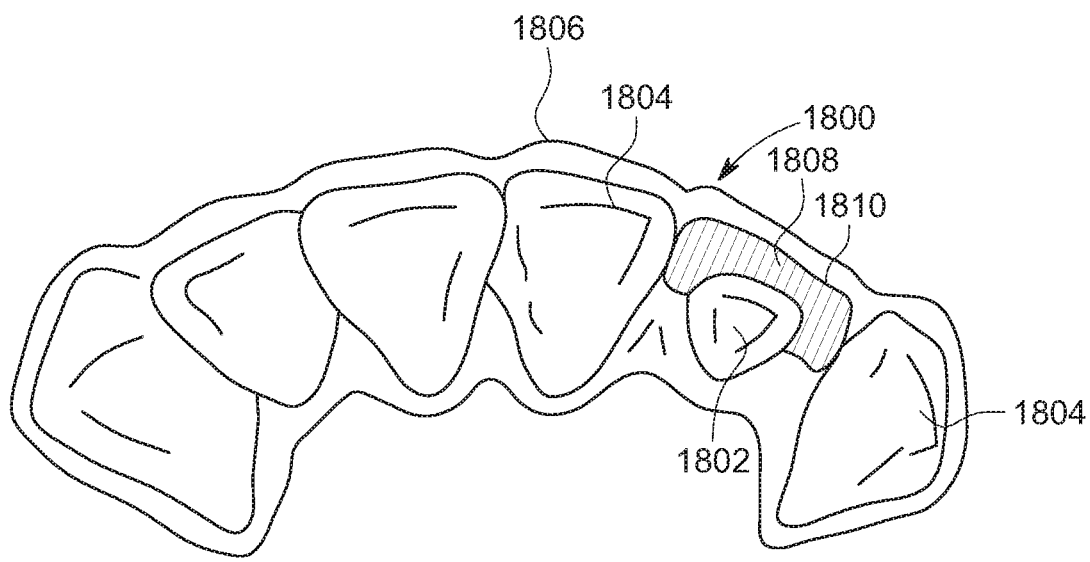
FIG. 18 illustrates an aligner assembly having a shell and a cap, in accordance with an embodiment of the present invention.

Referring to FIG. 18 an aligner assembly 1800 according to an alternative embodiment of the disclosure. The aligner assembly 1800 is adapted to apply force on a tooth 1802 that is misshaped and malformed and includes a shell 1806 and a cap 1808 disposed abutting a base wall 1810 of the shell 1806. Further, the cap 1806 is disposed in a cavity of the shell 1806 that corresponds to a cavity of the tooth 1802. The cap 1808 is adapted to contact the upper surface of tooth 1802 when the aligner assembly 1800 is positioned over the tooth 1802. In an embodiment, the cap 1808 may be removably attached to the inner surface of the base wall 1810. As the cap 1808 is affixed to the tooth 1802, the cap 1808 restores a correct size of the tooth 1802, thus allows the shell 1806 to apply corrective forces on the tooth 1802 to facilitate a reposition of the tooth 1806.

Figure 19:
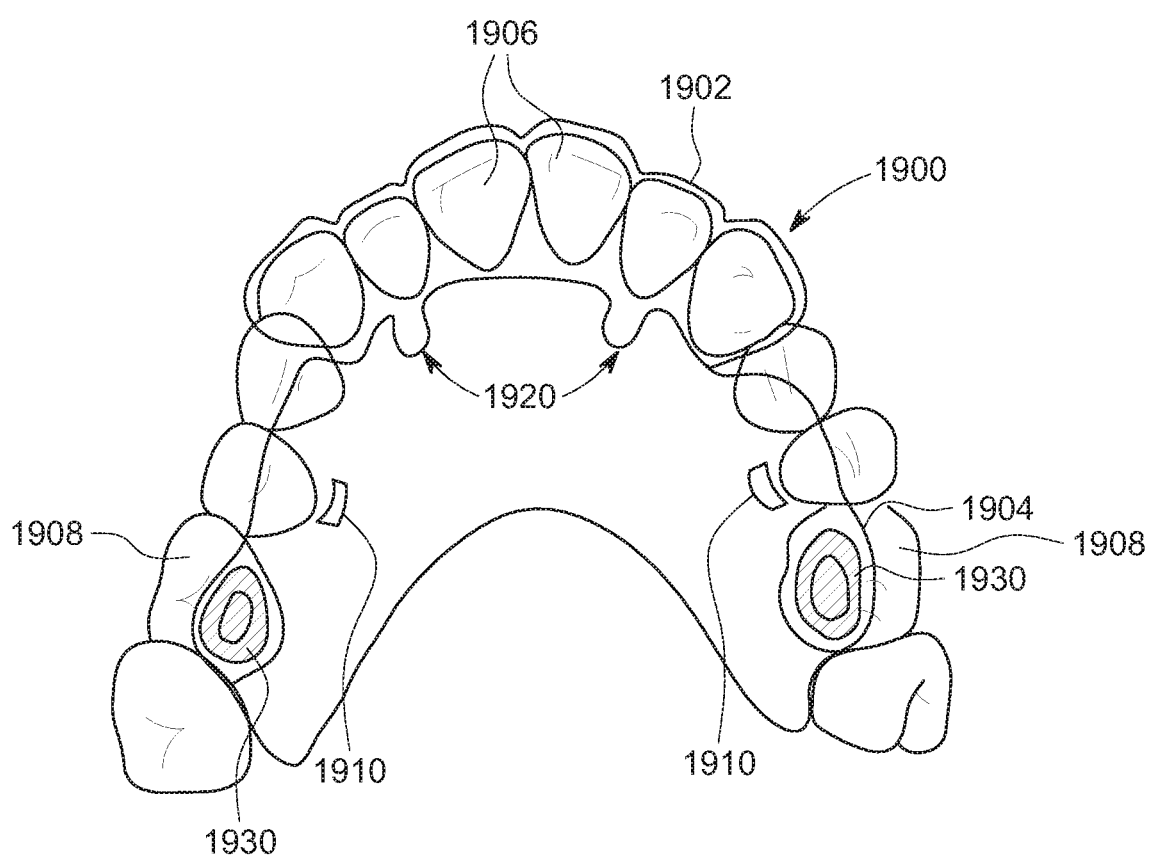
FIG. 19 illustrates an aligner assembly depicting a shell having a first segmented shell engaged to a second segmented shell, in accordance with an embodiment of the present invention.

Referring to FIG. 19, an exemplary shell 1900 having a plurality of segments, for example a first segment 1902 and a second segment 1904 adapted to be removably engaged/connected with the first segment 1902. The first segment 1902 may include one or more cavity for receiving one or more first teeth 1906 and is adapted to the align one or more teeth 1906. The second segment 1904 is configured to receive or engage one or more second teeth 1908. In an embodiment, a stiffness of the first segment 1902 of the shell 1900 may be lower than a stiffness of the second segment 1904. By using the second segment 1904 of relatively higher stiffness, a stabilization of the shell 1900 within the patient mouth and the teeth is facilitated. Further, the shell 1900 may include one or more grip members 1910 to facilitate a holding of the second segment 1904. Also, the shell 1900 includes one or more dovetail arrangement 1920 for engaging the first segment 1902 with the second segment 1904. Although, dovetail arrangement 1920 is contemplated, it may be envisioned that any other means or arrangement may be utilized for engaging first segment 1902 to the second segment 1904. Also, one or more bite blocks 1930 may be coupled to second segment 1904 of the shell 1900. As the bite blocks 1930 in the second segment 1904 are included in the second segment 1904 that is made of material having relatively higher stiffness, a wear rate of the bite blocks 1930 is reduced. Further, by constructing the second segment 1904 from a stiffer material, only the first segment 1902 is changed for incrementally moving the teeth 1906. In this manner, a reduction in overall material consumption is achieved.

Figure 20:
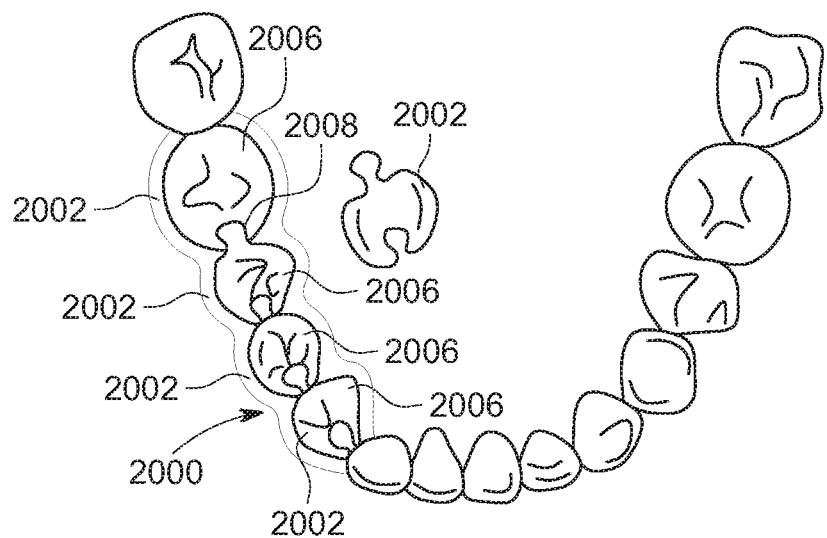
FIG. 20 illustrates a shell formed by attaching a plurality of segmented shells, in accordance with an embodiment of the present invention.

Referring to FIG. 20, another exemplary shell 2000 is shown. The exemplary shell 2000 includes a plurality of segments 2002, each segment 2002 having a cavity of receive a tooth 2004. Further, each segment 2002 is attached to an adjacent segment via dovetail arrangement 2008. Although, dovetail arrangement 2008 is contemplated, it may be envisioned that any other means or arrangement may be utilized for engaging the segments 2002. In an embodiment, the segments may be frictionally engaged with each other. Although, each segment 2002 is shown to receive a single tooth, it may be appreciated that the segment 2002 may receive any number of teeth. This allows for minimal use of plastic and only the segment corresponding to the tooth that needs incremental movement is changed.

Figure 21:
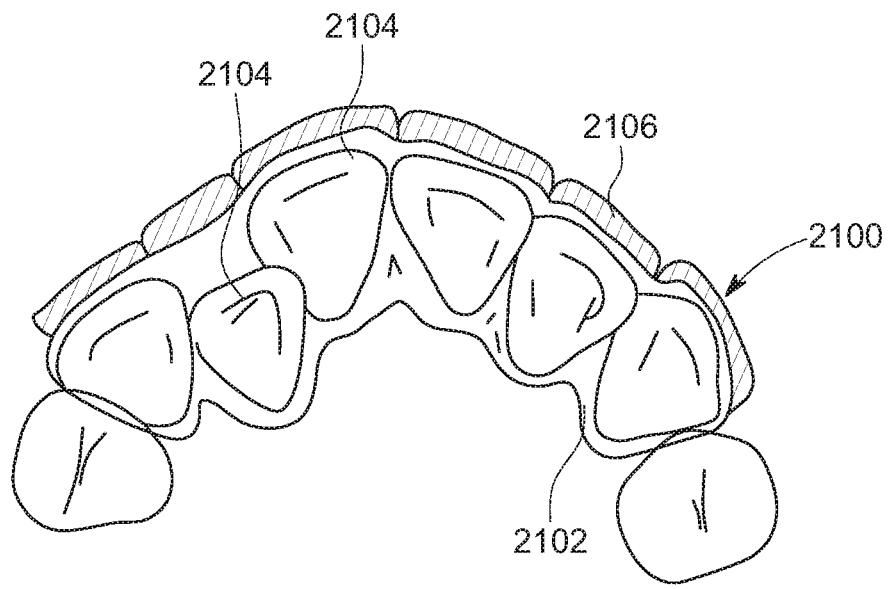
FIG. 21 illustrates an aligner assembly having a veneer attached to a shell, in accordance with an embodiment of the present invention.
Figure 22:
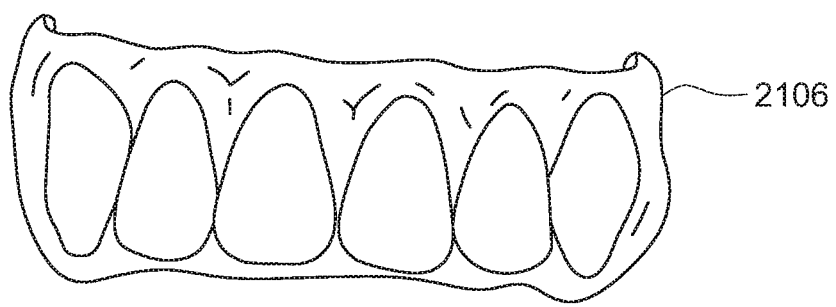
FIG. 22 illustrates the veneer of the aligner assembly of FIG. 21, in accordance with an embodiment of the present invention.

Referring to FIG. 21, an aligner assembly 2100 having a shell 2102 for facilitating an alignment of one or more teeth 2104, and a veneer 2106 attached to a front wall of the shell 2102 is shown. The veneer 2106 is adapted to be positioned on lingual or buccal side of the teeth 2104 and adapted to act as mask to make an appearance of the jaw more aesthetic. As shown in FIG. 22, the veneer 2100 may include a shape according to the teeth which needs to be masked. FIG. 21 depict the veneer 2106 positioned on the front side of shell 2102 so that the teeth 2104 can be hidden. In an embodiment, the veneer 2106 may be disposed inside the shell 2102, and may be positioned between the teeth 2104 and the front wall of the shell 2102. In an embodiment, the veneer 2106 matches a tooth color. In an embodiment, the veneer 2106 may formed along with the shell 2102 and may be directly printed on the shell 2102. In an embodiment, the veneer 2106 may be bonded to the shell 2102. In an embodiment, the veneer 2106 may be attached to the shell 2102 using pressure sensitive adhesive. The veneer 2106 masks the malocclusion of the one or more teeth 2104 as the one or more teeth 2014 are being corrected, making a treatment less noticeable and therefore increasing a compliance of the patient to the treatment. In an embodiment, the veneer 2106 may be used as shims to move the tooth along with augmenting aesthetics.

Figure 23:
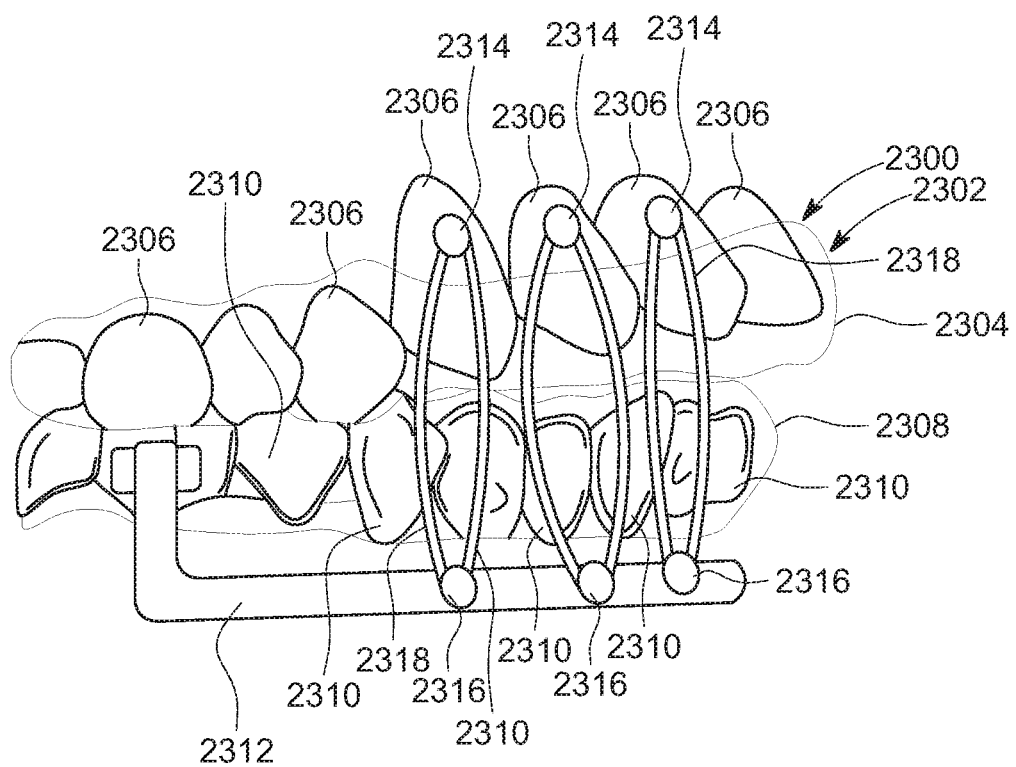
FIG. 23 illustrates an orthodontic appliance, in accordance with an embodiment of the present invention.

Referring to FIG. 23, an orthodontic appliance 2300 is shown. The orthodontic appliance 2300 includes an aligner assembly 2302 having a first shell 2304 adapted to receive one or more first teeth 2306 to facilitate extrusion of the one or more first teeth 2306, and is designed with the final shape of the aligner bypassing the need for incremental aligners. The first shell 2304 is used as a guide to move the first teeth 2306 along a predetermined path The aligner assembly 2300 also include a second shell 2308 adapted to receive one or more second teeth 2310 to facilitate an alignment of the one or more second teeth 2310. As shown, the one or more first teeth 2306 refers to one or more upper teeth, while the one or more second teeth 2310 refers to one or more lower teeth. The orthodontic appliance 2300 further includes an elongated shaft 2312 extending along a width of the lower teeth, and may be attached to the second shell 2308. Further, orthodontic appliance 2300 may include one or more first buttons 2314 coupled to the one or more first teeth 2306, and one or more second buttons 2316 attached to the elongated shaft 2312. In an embodiment, the one or more second buttons 2316 may be attached to the lower jaw, and in such a case, the elongated shaft 2312 may be omitted. Further, the orthodontic appliance 2300 may include one or more elastic members 2318 coupling the first button 2314 to the second button 2316. The elastic member 2318 that extends between the first button 2316 and the second button 2318 is disposed under tension, and hence applies a downward force on the corresponding first teeth 2306. As the downward force is applied on the first teeth 2306, the first shell 2304 guides the downward motion of the first teeth 2306 to the final position. In this manner, the orthodontic appliance 2300 may enable extrusion of one or more first teeth 2306. Further, it may be appreciated that the first shell 2304 is adapted to guide a downward movement of the one or more first teeth 2306 to final position due to the presence of gap/relief between a lower wall of the first shell 2304 and crowns of the one or more first teeth 2304. Further, aligner assembly 2302 may include one or more stabilizing attachments to facilitate a stabilization of the second shell 2308 on the one or more second teeth 2310 and to prevent an undesired removal of the second shell 2308. In an embodiment, the elongated shaft 2312 may formed into the second shell 2308. In such a case, the elongated shaft 2312 may be attached to the one or more teeth by cutting a window into the second shell 2308. Also, one or more bite blocks (not shown) can be built into the second shell 2308 to prevent a molar from moving upwards as a result of the reactive force.

Figure 24:
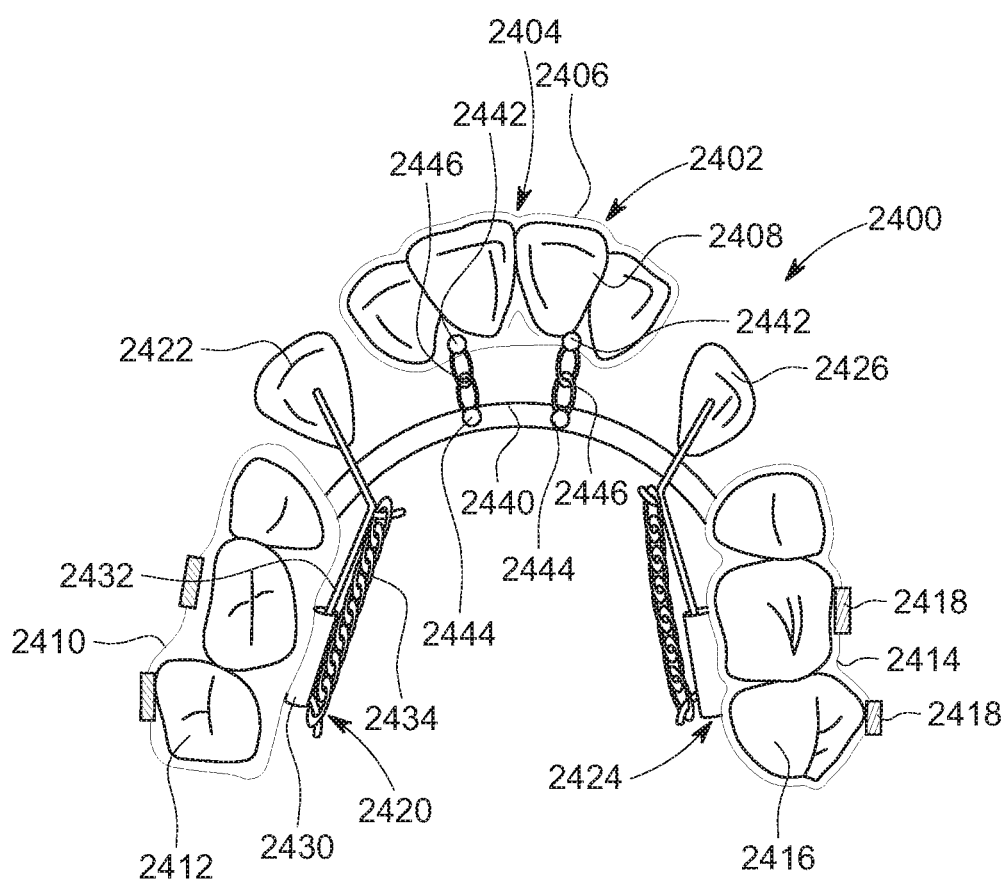
FIG. 24 illustrates an orthodontic appliance, in accordance with an embodiment of the present invention.

Referring to FIG. 24, an orthodontic appliance 2400 is shown. The orthodontic appliance 2400 includes an aligner assembly 2402 having a shell 2404 including a plurality of shell segments, for example, a first shell segment 2406 for receiving one or more front teeth 2408 (hereinafter referred to as one or more first teeth 2408), a second shell segment 2410 for receiving one or more second teeth 2412, and a third shell segment 2414 for receiving one or more third teeth 2416 disposed symmetrically opposite to the one or more second teeth 2412. The first shell segment 2406 is adapted to facilitate an alignment of the first teeth 2408, the second shell segment 2410 is adapted to facilitate an alignment of the second teeth 2412, and the third shell segment 2414 is adapted to facilitate an alignment of the third teeth 2416. In an embodiment, the second shell segment 2410 is only used for holding all the second teeth 2412 together. Similarly, in an embodiment, the third shell segment 2414 is only used for holding all the third teeth 2416 together. In an embodiment, the aligner assembly 2402 may include one or more fixation attachments 2418 for fixing and stabilizing a shell segment with one or more teeth, for example, the third shell segment 2414 with the third teeth 2416. Further, the orthodontic appliance 2400 may include one more telescopic assemblies, for example, a first telescopic assembly 2420 adapted to reduce a space between a fourth tooth 2422 and the second teeth 2412, and a second telescopic assembly 2424 adapted to reduce a space between a fifth tooth 2426 and the one or more third teeth 2416. The first telescopic assembly 2422 and the second telescopic assembly 2424 are similar in construction, function, and structure, and therefore, for the sake of clarity only the first telescopic assembly 2420 is explained.

The first telescopic assembly 2420 may include a first elongated receptacle 2430 having a tubular structure, and a first elongated member 2432 telescopically extending from the first elongated receptacle 2430 and adapted to slide relative to the first elongated receptacle 2430. As shown, the first elongated receptacle 2430 is coupled to the one or more second teeth 2412 via the second segmented shell 2410, while the first elongated member 2432 is attached to the fourth tooth 2422. Further, the first telescopic assembly 2420 includes a first elastic member 2434 extending between the first elongated receptacle 2430 and the first elongated member 2432 and coupled to the first elongated receptacle 2430 and the first elongated member 2432. The first elastic member 2434 is disposed under a tension, and therefore, applies a force on the first elongated receptacle 2430 and the first elongated member 2432 to move the first elongated receptacle 2430 and the first elongated member 2432 towards each other. In so doing, the fourth tooth 2422 is moved towards the one or more second teeth 2412, and hence reducing the space therebetween.

Additionally, or optionally, the orthodontic appliance 2400 may include an arch member 2440 extending substantially parallel to the first teeth 2408, one or more first buttons 2442 attached to the first shell segment 2440, and one or more second buttons 2444 attached to the arch member 2440. Also, one or more elastic bands 2446 extends between the one or more first buttons 2442 and the one or more second buttons 2444. The elastic band 2446 is coupled to the first button 2442 and the second button 2444, and is disposed under a tension. Therefore, the one or more elastic bands 2446 apply a force on the first teeth 2408 to facilitate intrusion. In this manner, by using the segmented shells in an aligner assembly one can overcome the deficiencies in the use of the aligner assemblies specifically in reducing space between teeth, intrusion of one or more teeth, etc. Further, this configuration also limits the number of segmented shells to be used through am entire course of treatment and also provides more predictable controlled forces.

Figure 25:
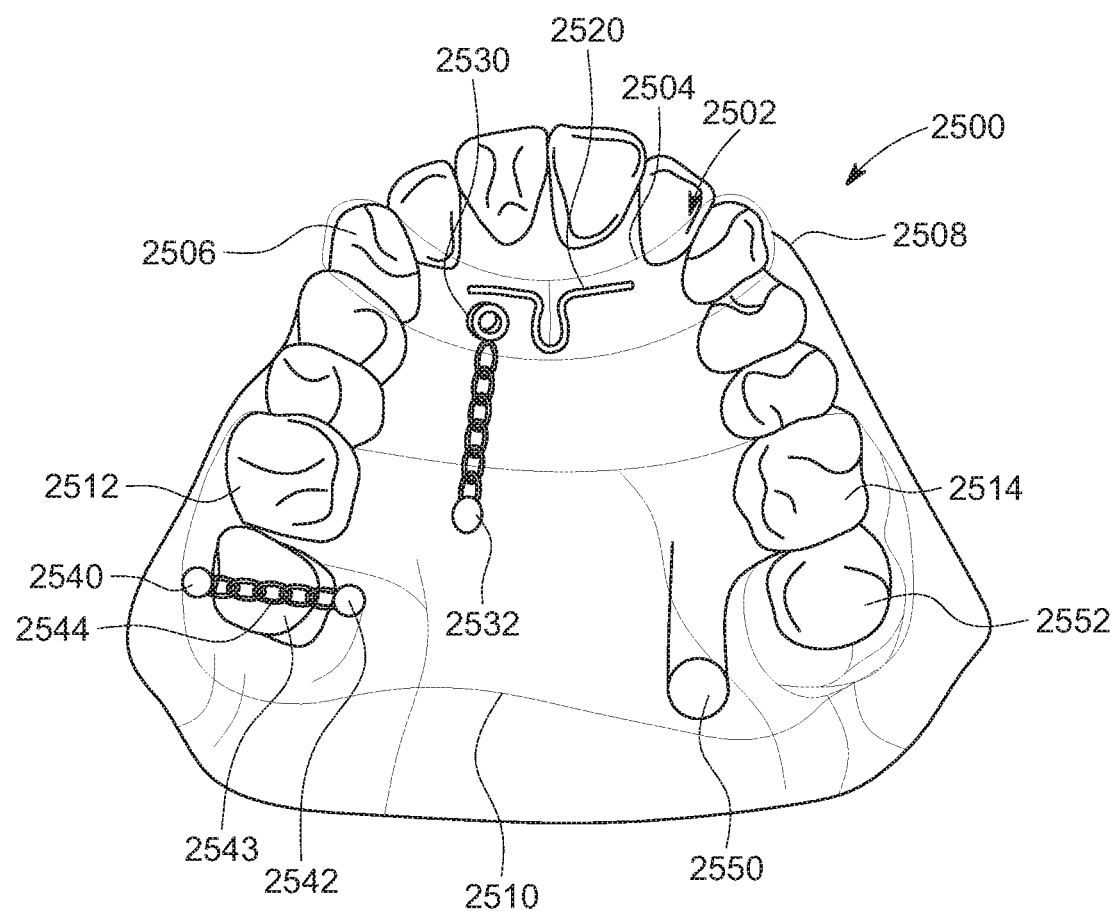
FIG. 25 illustrates an orthodontic appliance, in accordance with an embodiment of the present invention.

Referring to FIG. 25, an orthodontic appliance 2500 is shown. The orthodontic appliance 2500 includes a shell 2502 having a first shell segment 2504 configured to receive a first tooth 2506 and a second tooth 2508 disposed symmetrically opposite to the first tooth 2506, and a second shell segment 2510 configured to receive one or more third teeth 2512 and one or more fourth teeth 2514 disposed symmetrically opposite to the one or more third teeth 2512. Further, the orthodontic appliance 2500 may include a looped wire 2520 attached to a middle portion of the first shell segment 2504. The looped wire 2520 is adapted to apply a force on the first tooth 2506 and the second tooth 2508 to facilitate a movement of the first tooth 2506 and the second tooth 2508 towards each other or away from each other.

In an embodiment, the orthodontic appliance 2500 may include a first button 2530 attached to the first shell segment 2504 and a second button 2532 attached to the second shell segment 2510. Further, a first elastic member 2534 may be coupled to the first button 2530 and the second button 2532. The first elastic member 2534 may extend from the first button 2530 to the second button 2532 and may be disposed under a tension. Due to the presence or tension in the first elastic member 2534, the first shell segment 2504 and the second shell segment 2510 may move towards each other, thereby facilitating a reduction in space between the first tooth 2506 and the one or more third teeth 2512.

Figure 26A:
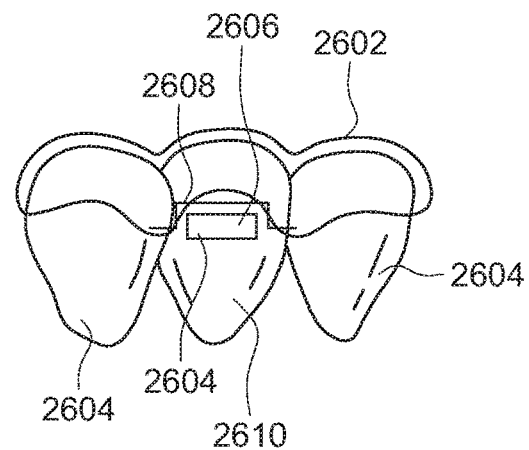
FIG. 26A illustrates an aligner assembly disposed on one or more teeth and depicting an initial position of the one or more teeth, in accordance with an embodiment of the present invention.
Figure 26B:
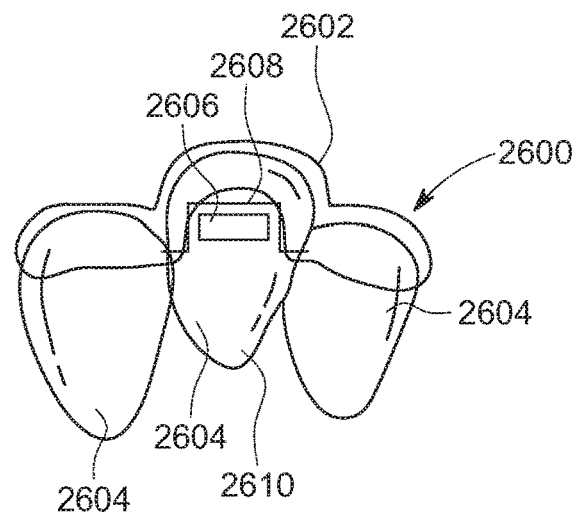
FIG. 26B illustrates the aligner assembly disposed on one or more teeth and depicting a final position of the one or more teeth, in accordance with an embodiment of the present invention.
Figure 26C:
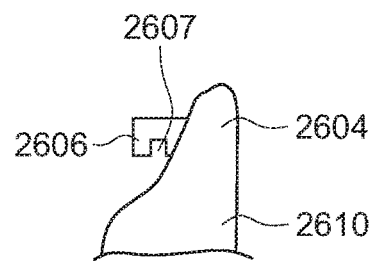
FIG. 26C illustrates a bracket of the aligner assembly attached to the tooth, in accordance with an embodiment of the present invention.

Additionally, or optionally, the orthodontic appliance 2500 may include a third button 2540 attached to a tooth 2543 and a fourth button 2542 disposed on opposite side of the tooth and attached to the second shell segment 2510. Further, a second elastic member 2544 may be coupled to the third button 2540 and the fourth button 2542, and applies a force on the tooth 2543. Due to the force applied by the second elastic member 2544, an intrusion of the tooth 2543 may be facilitated. Additionally, or optionally, the orthodontic appliance 2500 may include a metallic spring 2550 attached to the second shell segment 2510 and a tooth 2552 to facilitate a backward movement of the tooth 2552. By using various attachment to create hybrid structures more controlled and predictable forces may be applied on the teeth, thus enable more efficient concurrent and limited attachments and cost-effective treatment of teeth. Since multiple concurrent movement are facilitated, a need to change the shells is reduces, thereby reducing overall material, such as, plastic, during the course of treatment, Referring to FIGS. 26A, 26B, and 26C, an aligner assembly 2600 is shown that may be suitable for a lower jaw. The aligner assembly 2600 includes a shell 2602 having one or more cavities for receiving one or more teeth 2604. The aligner assembly 2600 further includes one or more brackets 2606 attached to the one or more teeth 2604. It may be appreciated that a single bracket is attached to single tooth. Further, each bracket 2606 includes a slot 2607 to receive a wire 2608 attached to or embedded in the shell 2602. The wire 2608 is adapted to apply a force on the bracket 2606 in an upward direction to facilitate an extrusion of a tooth 2610. FIG. 26A shows an initial position of the tooth 2610, while FIG. 26B illustrates a final position of the tooth 2610. In an embodiment, the wire 2608 may be made of a shape memory alloy. Further, an orientation of the slot 2607 and a positioning of bend in the wire 2608 may be selected based on a desired direction of tooth movement. The wire 2608 may be directly attached to the bracket 2606, or held with a self-ligating system, or a snap fit assembly disposed in the bracket 2606 may be utilized.

Figure 27:
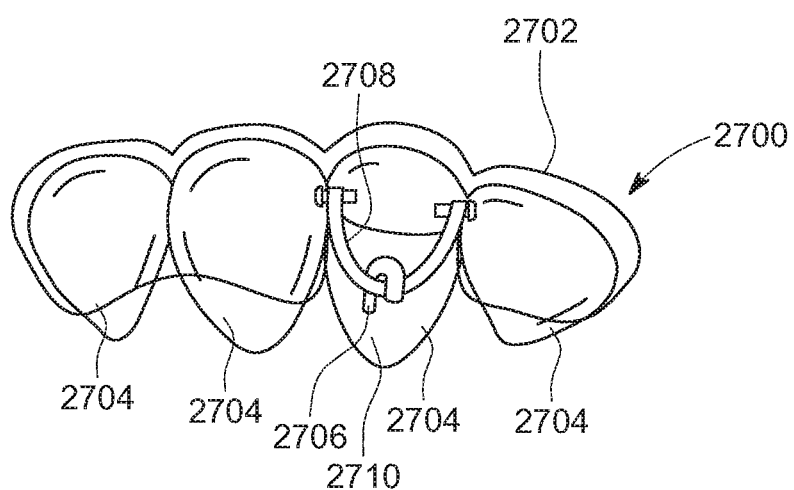
FIG. 27 illustrates an aligner assembly, in accordance with an embodiment of the present invention.

Referring to FIG. 27, an aligner assembly 2700 is shown. The aligner assembly 2600 includes a shell 2702 having one or more cavities for receiving one or more teeth 2704. The aligner assembly 2700 further includes one or more hooks 2706 attached to the one or more teeth 2704. It may be appreciated that a single hook may be attached to a single tooth. Further, each hook 2706 is adapted to engaged with a wire 2708 attached to or embedded in the shell 2702. In an embodiment, the wire 2708 may include an arcuate shape. In some implementations, the wire 2708 may be mechanically attached, or crimped, or riveted to the shell 2702. Alternatively, the wire 2708 may be received in tubes attached to the shell 2702. The wire 2708 is adapted to swing upward and to produce a torqueing couple on the tooth 2704. Further, the wire 2708 may be positioned inside one or more self-ligating brackets or snap fit bracket slots. Further, the aligner assembly 2700 may include one or more stabilizing attachments that engage the shell 2702 to stabilize the shell 2702 with the one or more teeth 2704. The aligner assembly 2700 provides predictable torqueing forces to the one or more teeth 2704, and limits the number of aligner changes and attachments since the relatively higher range of activation and elasticity.

Figure 28A:
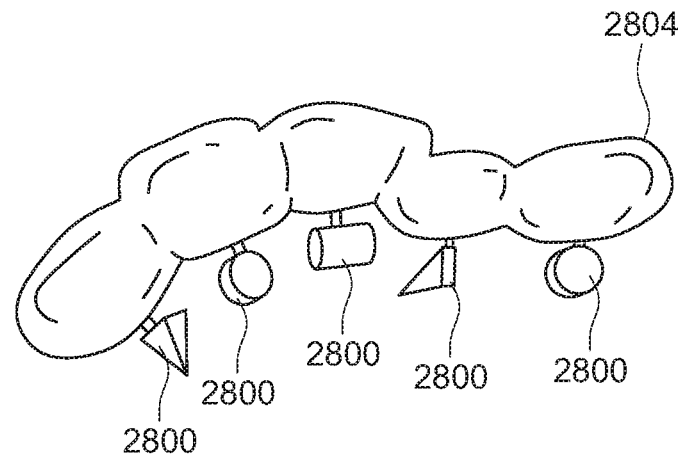
FIG. 28A illustrates one or more engagement structures attached to a tray, in accordance with an embodiment of the present invention.
Figure 28B:
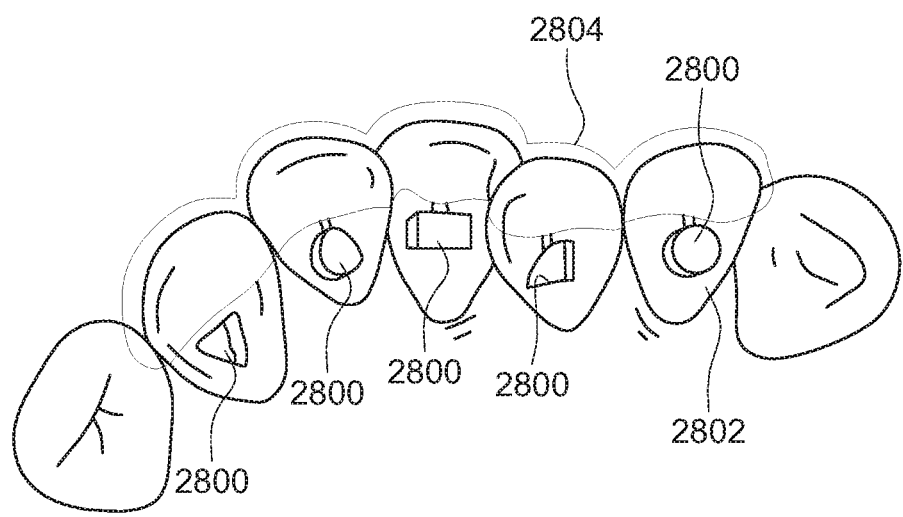
FIG. 28B illustrates the tray of FIG. 28A mounted on one or more teeth for attaching the engagement structures on the one or more teeth, in accordance with an embodiment of the present invention.

FIGS. 28A and 28B show a carrier tray 2804 to accurately locating and bonding one or more engagement structures 2800 on one or more teeth 2802. The engagement structures 2800 and the carrier tray 2804 are printed as one unit from the same material. The tray 2800 has one or more cavities to receive the one or more teeth and facilitates locating the one or more engagement structures 2800 on the one or more teeth 2802. Once located on the corresponding tooth, the one or more engagement structures 2800 are bonded directly to the tooth in their correct position by means known by those skilled in the art. Thereafter, the one or more engagement structures 2800 are detached from the carrier tray 2804 by snipping.

The engagement structures 2800 may be pre-pasted with ultraviolet light, or chemical adhesive, or with any other techniques known well by those skilled in the art. The engagement structures having precoated adhesive need to be packaged in a carton that prevents the penetration of light, minimizing or eliminating an exposure to the light and doesn't allow light to penetrate the carton to prevent premature curing. In an embodiment, the engagement structures 2800 can be changed during the treatment. The engagement structures 2800 are designed using computer aided design tools and printed using additive manufacturing technique, such as 3D printing on the tray 2804, subtractive milling techniques, or any other technique well known in the art.

Figure 29:
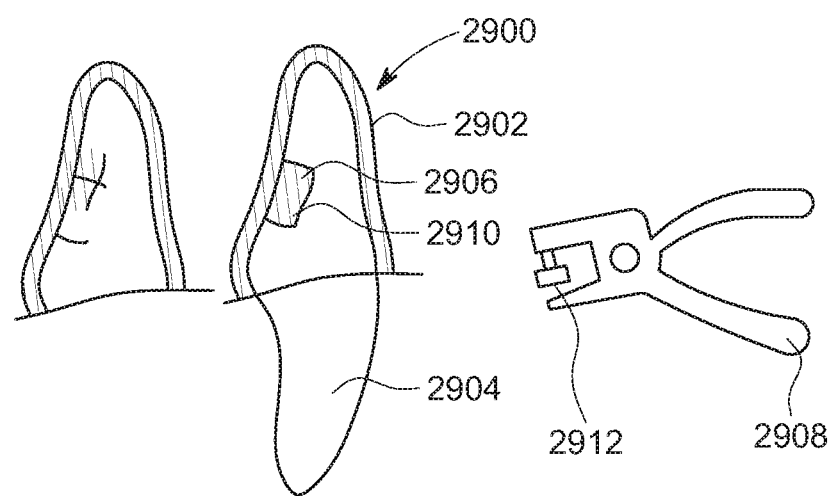
FIG. 29 illustrates an aligner assembly having a shell and a plier used for forming an engagement structure on the shell, in accordance with an embodiment of the present invention.

Referring to FIG. 29, an aligner assembly 2900 having a shell 2902 is shown. The shell 2902 may include one or more cavities to receive one or more teeth 2904. The shell 2902 may include one or more portions 2906 of thermo plastic materials or deformable plastic materials and may include a marker corresponding to each portion. A doctor may deform the portion by using a plier 2908 to form an engagement structure 2910 on an inner surface of the shell 2902 that may apply a force on the tooth 2904 to reposition the tooth 2904. In this manner, the aligner assembly 2900 may facilitate a formation of desired engagement structures 2906 at the chair side. The plier 2908 may include a customized or a series of standardized shapes forming tool 2912 removably attached to a frame of the plier 2908. The forming tool 2912 can be changed to form the engagement structure 2906 of a desired shape and size. The forming tool 2912 can be printed or milled, and the plier 2908 may be used to mechanically or thermo-mechanically deform the shell 2902 to form the desire shape and structure of the engagement structure 2906.

Further, it may be appreciated that any component of the aligner assemblies or the orthodontic appliances, for example, the shell discussed above designed and/or manufactured using one or more computed aided technologies known in the art. However, other designing and manufacturing technologies for designing and making one or more components of the aligner assemblies and/or the orthodontic appliances are also envisioned and do not limit the scope of the disclosure.

In an exemplary embodiment, for manufacturing one or more components of any of the aligner assembly discussed above, a 3-dimensional virtual model of each tooth is made by scanning a mouth of the patient. The model allows for moving the one or more teeth to set the one or more teeth into the final positions. Thereafter, using reverse engineering techniques with linear and non-linear movement, stages and sequencing of teeth movements are planned. Further, for each incrementally planned event, a model may be printed using additive printing technology and the component, for example, shell, is formed using any manufacturing technique, such as, thermoforming, 3d printing, etc. formed on each of these models using a thermos plastic material.

Further, one or more components of various aligner assemblies and orthodontic appliances may be electroplated with materials, such as, but not limited to, titanium, stainless steel, etc., for increasing strength and resistance to fatigue or failure In an embodiment, a thickness of the electroplating may range from 10 microns to 100 microns. In an embodiment, one or more components of various aligner assemblies and orthodontic appliances may be coated with stronger polymers or composites by common techniques known by those skilled in the art.

What is claimed is:

1. An aligner assembly for facilitating an alignment of one or more teeth, the aligner assembly comprising:
    an inner shell comprising an exterior surface and an interior surface, wherein the interior surface of the inner shell is adapted to engage one or more teeth;
    an outer shell comprising an exterior surface and an interior surface, wherein the interior surface of the outer shell engages the exterior surface of the inner shell;
    a first protruding member comprising a first shape and disposed on the exterior surface of the inner shell, wherein the first protruding member engages and abuts against the interior surface of the outer shell, such that the interior surface of the inner shell is adapted to apply a force to the one or more teeth; and
    a second protruding member comprising a second shape and disposed on the exterior surface of the inner shell, wherein the second shape is independent of the first shape, and wherein the second protruding member engages and abuts against the interior surface of the outer shell, such that the interior surface of the inner shell is adapted to apply a force to the one or more teeth.

2. The aligner assembly of claim 1, wherein the aligner assembly further comprises one or more cooperating structures coupled with other of the one or more teeth and the inner or outer shells, wherein each cooperating structure is adapted to engage the first or second protruding members to facilitate a repositioning of the one or more teeth.

3. The aligner assembly of claim 1, wherein the first or second protruding members are each adapted to be removably attached to the one of the one or more teeth or the inner or outer shells.

4. The aligner assembly of claim 1, wherein the outer shell further comprises a recess for receiving either the first or second protruding members of the inner shell.

5. The aligner assembly of claim 1 wherein the inner or outer shell includes a coating to facilitate a reduction of at least one of halitosis or a decalcification of the one or more teeth.

6. An aligner assembly for facilitating a repositioning of one or more teeth, the aligner assembly comprising:
    an inner shell comprising an exterior surface and an interior surface, wherein the interior surface of the inner shell is adapted to engage one or more teeth;
    an outer shell comprising an exterior surface and an interior surface, wherein the interior surface of the outer shell engages the exterior surface of the inner shell; and a first protruding member comprising a first shape having an asymmetrical cross-section configuration and disposed on the exterior surface of the inner shell, wherein the first protruding member engages and abuts against the interior surface of the outer shell, such that the interior surface of the inner shell is adapted to apply a force to the one or more teeth.

7. The aligner assembly of claim 6, further comprising one or more cooperating structures coupled to the outer shell and adapted to engage with the first protruding member to facilitate a reposition of the one or more teeth.

8. The aligner assembly of claim 7, wherein the outer shell further comprises a recess for receiving either the first or second protruding members of the inner shell.

9. The aligner assembly of claim 7, wherein the first protruding member extends from the exterior surface of the inner shell and the one or more cooperating structures extend from the interior or exterior surface of the outer shell.

10. The aligner assembly of claim 6 wherein the inner shell includes a coating to facilitate a reduction of at least one of halitosis or a decalcification of one or more teeth.

11. An orthodontic appliance, the orthodontic appliance comprising:

an inner shell comprising an exterior surface and an interior surface, wherein the interior surface of the inner shell is adapted to engage one or more teeth;

an outer shell comprising an exterior surface and an interior surface, wherein the interior surface of the outer shell engages the exterior surface of the inner shell;

a first protruding member comprising a first shape having an asymmetrical cross-sectional configuration and disposed on the exterior surface of the inner shell, wherein the first protruding member engages and abuts against the interior surface of the outer shell, such that the interior surface of the inner shell is adapted to apply a force to the one or more teeth; and a second protruding member comprising a second shape having a circular configuration and disposed on the exterior surface of the inner shell, and wherein the second protruding member engages and abuts against the interior surface of the outer shell, such that the interior surface of the inner shell is adapted to apply a force to the one or more teeth.

* * * * *